(12) United States Patent
Rowe et al.

(10) Patent No.: US 7,011,826 B1
(45) Date of Patent: *Mar. 14, 2006

(54) CONTROL OF ACIDOSIS

(75) Inventors: James Barber Rowe, Armidale (AU); Rafat A M Al Jassim, Gatton (AU)

(73) Assignee: The University of New England, New South Wales (AU)

( * ) Notice: Subject to any disclaimer, the term of this patent is extended or adjusted under 35 U.S.C. 154(b) by 321 days.

This patent is subject to a terminal disclaimer.

(21) Appl. No.: 09/786,253

(22) PCT Filed: Jul. 3, 2000

(86) PCT No.: PCT/AU00/00805

§ 371 (c)(1),
(2), (4) Date: Aug. 15, 2001

(87) PCT Pub. No.: WO01/02008
PCT Pub. Date: Jan. 11, 2001

(30) Foreign Application Priority Data

Jul. 2, 1999 (AU) .................... PQ1376

(51) Int. Cl.
A61K 38/16 (2006.01)
A61K 38/00 (2006.01)
A61K 31/70 (2006.01)

(52) U.S. Cl. ............... 424/93.1; 424/93.3; 424/94.4; 424/93.45; 424/93.41; 514/152; 514/200; 514/31; 514/311; 514/37; 514/54; 514/770; 514/8; 514/9; 435/252.9; 435/853

(58) Field of Classification Search ............ 514/6, 514/8, 9, 31, 37, 54, 152, 200, 311, 866, 903, 514/951, 110, 120, 725, 784, 785, 770; 435/93.45, 435/93.44, 196, 183, 195; 424/243.1, 234.1, 424/279.1, 150.1, 165.1, 820, 180, 94.6, 424/93.44, 520, 490, 725, 780, 93.41, 93.1, 424/93.3, 93.4, 93.45; 536/123.1

See application file for complete search history.

(56) References Cited

U.S. PATENT DOCUMENTS 4,061,732 A * 12/1977 Muir et al. ............... 424/117
4,112,069 A * 9/1978 Huber ...................... 424/93.4
4,203,968 A 5/1980 Harris et al.
4,237,116 A * 12/1980 Gillin et al. .............. 424/117

(Continued)

FOREIGN PATENT DOCUMENTS

WO    WO 96 28177    9/1996

(Continued)

OTHER PUBLICATIONS

Genbank Accession No. AB002514 Steptococcus equinus DNA for 16S rRNA, strain NCTC 9814 13 Feb. 1999.

(Continued)

Primary Examiner—Lynette R. F. Smith
Assistant Examiner—Ginny Allen Portner
(74) Attorney, Agent, or Firm—McDonnell Boehnen Hulbert & Berghoff LLP.

(57) ABSTRACT

The present invention relates to a vaccine for the prevention of lactic acidosis in a vertebrate, said vaccine comprising at least one isolated microorganism, or fragment or fragments thereof, wherein said microorganism is capable of producing lactic acid within the gut of said vertebrate, and wherein said microorganism is selected from the group consisting of: Clostridium-like species, Prevotella-like species, Bacteroides-like species, Enterococcus-like species, Selenomonas species, non-dextran slime producing Streptococcus species and non-slime producing lactic acid bacterial isolates.

12 Claims, 1 Drawing Sheet

U.S. PATENT DOCUMENTS

| | | | | |
|---|---|---|---|---|
| 4,276,286 | A | * | 6/1981 | Ishihara et al. ............. 424/117 |
| 4,382,097 | A | * | 5/1983 | Vedamuthu et al. .......... 426/43 |
| 4,393,046 | A | * | 7/1983 | Baylis et al. ................ 424/117 |
| 4,394,377 | A | * | 7/1983 | Spires ........................ 514/459 |
| 4,579,733 | A | * | 4/1986 | Kawai et al. ............ 424/93.44 |
| 4,582,798 | A | | 4/1986 | Brown et al. |
| 4,710,379 | A | * | 12/1987 | Kawai et al. ............ 424/93.44 |
| 4,746,512 | A | * | 5/1988 | Kawai et al. ............ 424/203.1 |
| 4,906,612 | A | * | 3/1990 | Hayashi et al. ................ 514/8 |
| 5,055,455 | A | * | 10/1991 | Pier ............................ 514/54 |
| 5,290,767 | A | * | 3/1994 | Rowe ........................... 514/30 |
| 5,380,525 | A | * | 1/1995 | Leedle et al. ............. 424/93.4 |
| 5,529,793 | A | * | 6/1996 | Garner et al. ................ 426/61 |
| 5,534,271 | A | * | 7/1996 | Ware et al. .................... 426/2 |
| 5,695,984 | A | * | 12/1997 | Argoudelis et al. ...... 435/253.5 |
| 5,939,303 | A | * | 8/1999 | Cheng et al. ............... 435/196 |
| 5,980,910 | A | * | 11/1999 | Pier ........................ 424/244.1 |
| 5,981,234 | A | * | 11/1999 | Argoudelis et al. ........ 435/71.3 |
| 6,303,572 | B1 | * | 10/2001 | Rowe ............................. 514/6 |
| 6,429,006 | B1 | * | 8/2002 | Porro et al. ........................ 1/1 |
| 6,468,964 | B1 | * | 10/2002 | Rowe ............................. 514/6 |
| 6,524,574 | B1 | * | 2/2003 | Spangler et al. ........... 424/93.3 |
| 6,613,549 | B1 | * | 9/2003 | Reid et al. ............... 424/93.45 |
| 6,743,431 | B1 | * | 6/2004 | Pier ........................ 424/243.1 |

FOREIGN PATENT DOCUMENTS

| | | | |
|---|---|---|---|
| WO | | 97/14802 | * 4/1997 |
| WO | | 99/00136 | * 1/1999 |
| WO | WO 99/12564 | A1 | 3/1999 |
| WO | WO 99 20739 | | 4/1999 |

OTHER PUBLICATIONS

Genbank Accession No. AF104109 *Streptococcus bovis* strain JB1 16s ribosomal RNA gene, partial sequence Feb. 28, 1999.

Genbank Accession No. AB009188 Unidentified rumen bacterium RFN3 gene for 16S ribosomal RNA, partial sequence Dec. 18, 1997.

J. Dairy Science 79(8), pp. 1467-1475 (1996) Krause, d0 and Russell, JB "How many ruminal bacteria are there?".

Genbank Accession No. M58835 *Streptococcus bovis* 16S ribosomal RNA Apr. 27, 1993.

Genbank Accession No. M62702 *Selenomonas ruminantium* (strain GA192) 16S ribosomal RNA Jun. 30, 1993.

Appl. Environ. Microbiol. 53(7), pp. 1620-1625 (1987) Nagaraja, T.G. and Taylor, M.B. "Susceptibility and resistance of ruminal bacterial to antimicrobial feed additives."

Environ. Microbiol. 54(12), pp. 2981-2985 (1988) Newbold, C.J. and Wallace, R.J. "Effects of the ionophores monensin and tetronasin on simulated development of ruminal lactic acidosis in vitro."

Shu Q. et al., "Immunisation against lactic acidosis in cattle", Research in Veterinary Science, vol. 67, No. 1, Aug. 1000, pp. 65-71, XP002312760 ISSN: 0034-5288.

Gill Harsharnjit S. et al., "Immunization with *Streptococcus bovis* Protects Against Lactic Acidosis in Sheep" Vaccine, vol. 18, No. 23, May 2000, pp. 2541-2548 XP004195919, ISSN 0264-410X.

* cited by examiner

CONTROL OF ACIDOSIS

TECHNICAL FIELD

The present invention relates to the identification of a series of microorganisms involved in the development of acidosis, together with the treatment and/or prevention and/or detection of acidosis in vertebrates, in particular, vaccines, compositions and methods for the treatment and/or prevention and/or detection of acidosis in vertebrates.

BACKGROUND ART

The over production of acid in the gut of an animal by microorganisms can cause fermentative acidosis, wherein is defined as a condition of abnormally high acidity in the gut that can lead to local and systemic acidosis, damage to the integrity of the gut wall and increased pathogenicity of gut bacteria and parasites.

The introduction of starch, sugars or oligosaccharides into the rumen of ruminant animals and the hind gut (caecum and colon) of ruminant and non-ruminant animals including humans, leads to rapid fermentation and production of volatile fatty acids (VFA). As the rate of VFA production exceeds their rate of removal, the pH may fall below 6.0, such that lactobilli take over, fermenting the starch to produce more lactic acid and creating an even lower pH (e.g. below 5.5). This is the scenario often presented to describe the sequential reactions in the rumen or the hind gut that lead to fermentative acidosis. The conditions of acidosis can be acute, posing an immediate life-threatening situation, or chronic (sub-acute), resulting in reduction in both feed intake and weight gain. There are also numerous disease conditions that can develop as secondary and tertiary consequences of acid accumulation in the gut.

Among the several methods for reducing the risk of acidosis, the use of antibiotic feed additives such as virginiamycin or certain ionophores have been relatively effective. However, under certain feeding conditions addition of virginiamycin has not always reduced the risk of acidosis (Godfrey et al., 1995; Courtney and Seirer, 1996; Thomiley et al., 1998).

Accordingly, there is a need to provide alternative means of controlling fermentative acidosis.

The main bacterial species and strains identified in the present invention, *Clostridium*-like species, *Prevotella*-like species, *Bacteroides*-like species, *Enterococcus*-like species, *Selenomonas* species, non-dextran slime producing *Streptococcus* species and non-slime producing lactic acid bacterial isolates, have not previously been considered to be important organisms in the development of fermentative acidosis. In fact, in the case of *Selenomonas ruminantium* it should be noted that the isolate selected by Leedle (1970) was identified on the basis of its ability to utilise lactic acid, rather than produce it and is therefore very different to the isolates that form part of the present invention.

Therefore, the present invention has identified a series of microorganisms responsible for the development of acidosis and describes vaccines, compositions and methods for the treatment and/or prevention and/or detection of acidosis in vertebrates.

DETAILED DESCRIPTION OF THE INVENTION

1. Vaccine/Pharmaceutical Compositions for Control of Acidosis

According to a first embodiment of the invention, there is provided a vaccine for the prevention of lactic acidosis in a vertebrate, said vaccine comprising at least one isolated microorganism, or fragment or fragments thereof, wherein said microorganism is capable of producing lactic acid within the gut of said vertebrate, and wherein said microorganism is selected from the group consisting of: *Clostridium*-like species, *Prevotella*-like species, *Bacteroides*-like species, *Enterococcus*-like species, *Selenomonas* species, non-dextran slime producing *Streptococcus* species and non-slime producing lactic acid bacterial isolates.

Typically, in the vaccine of the present invention, the microorganism forms part of the normal gut flora of a vertebrate. More typically, the microorganism is involved in the aetiology of fermentative lactic acidosis in vertebrates. Still more typically, the microorganism is selected from the group consisting of: *Streptococcus equinus, Clostridium*-like *vitulinus, Selenomonas ruminantium, Prevotella*-like species, *Bacteroides*-like species, *Enterococcus*-like species, *Streptococcus bovis* SbR1 and non-slime producing lactic acid bacterial isolates LAB02, LAB06 and LAB08. Yet still more typically, the microorganism is selected from the group consisting of: *Streptococcus bovis* (SbR1), *Streptococcus equinus* (SER1); *Streptococcus equinus* (SER2); *Selenomonas ruminantium* (SRR1); *Selenomonas ruminantium* (SRR3); *Clostridium*-like *vitulinus* (LVR3); *Clostridium*-like *vitulinus* (LVR4).

Yet even still more typically, the microorganism is one of the following strains deposited with the Australian Government Analytical Laboratories (AGAL) of 1 Suakin Street, Pymble, New South Wales, Australia, on 24 Jun. 1999 and given accession numbers as outlined in the following table:

| Microorganism | Accession number |
| --- | --- |
| *Streptococcus bovis* (SbR1 A2): | NM99/04455 |
| *Streptococcus equinus* (SER1): | NM99/04456 |
| *Streptococcus equinus* (SER2): | NM99/04457 |
| *Selenomonas ruminantium* (SRR1) | NM99/04458 |
| *Selenomonas ruminantium* (SRR3) | NM99/04460 |
| *Clostridium*-like *vitulinus* (LVR3) | NM99/04461 |
| *Clostridium*-like *vitulinus* (LVR4) | NM99/04462 |

Alternatively, the microorganism is one of the following strains deposited with the Australian Government Analytical Laboratories (AGAL) of 1 Suakin Street, Pymble, New South Wales, Australia, on 29 Jun. 2000 and given accession numbers as outlined in the following table:

| Lab. code | Description | Accession No. |
| --- | --- | --- |
| LAB 01/07-3 | *Prevotella*-like, short rods arranged in short chains and filaments. Gram positive | NM00/12630 |
| LAB 02/11-2 | non-slime producing lactic acid bacterial isolate, short straight rods with round ends, also long thin rods | NM00/12631 |
| LAB 03/D35 | *Prevotella*-like, predominantly rods in filaments. Gram+ | NM00/12632 |
| LAB 04/D37 | Non-dextran slime producing *Streptococcus* isolate predominantly large cocci. occurring mainly in pairs and singly (larger than the *S. bovis* isolates SB R1 or Sb5) | NM00/12633 |
| LAB 05/D23 | *Bacteroides*-like predominantly small cocci < than 1 $\mu$m in diameter mainly as diplococci: all Gram positive | NM00/12634 |
| LAB 06/D29 | Non-slime producing lactic acid bacterial isolate. long > than 5 $\mu$m thick rods, in singles and short chains | NM00/12635 |

-continued

| Lab. code | Description | Accession No. |
|---|---|---|
| LAB 07/H1 | *Bacteroides*-like, predominantly short rods forming filaments. Morphologically similar to those isolated from pigs (LAB01/07-3) | NM00/12636 |
| LAB 08/H15 | Non-slime producing lactic acid bacterial isolate. an endospore-forming bacteria. rod shaped. straight with a terminal spores. The spores are cylindrical. oval and round in shape, Gram positive | NM00/12637 |

*Clostridium*-like *vitulinus* (LVR3) and *Clostridium*-like *vitulinus* (LVR4) are new isolates. In relation to this, the 16S rRNA gene sequencing data as provided in the sequence listing (SEQ ID NOS: 1–7) of the present invention makes it clear that the organism is not a *Lactobacillus* and that it is closer to a *Clostridium*. However, it is not a spore-forming bacterium and cannot be classified as a member of the genus *Clostridium* per se. Consequently, it is necessary to name a new genus to cover the species *vitulinus,* and throughout the present specification, the organism is referred to as *Clostridium*-like *vitulinus*.

Further, in *Streptococcus bovis* (SbR1) (NM99/04455) strain of the present invention is distinct from other *Streptococcus bovis* strains, such as *Streptococcus bovis* (Sb5) (N94/8225), deposited with the Australian Government Analytical Laboratories (AGAL) of 1 Suakin Street, Pymble, New South Wales, Australia, on 8 Mar. 1994 strain, on the basis of a number of differentiating factors. For instance, the *Streptococcus bovis* (SbR1) (NM99/04455) strain produces far less dextran exudative slime material than for example, *Streptococcus bovis* Sb5. Lack of dextran slime formation has important implications for the antigenicity and for vaccine production since the slime makes harvesting of the cells considerably more difficult. For example, in the case of *Streptococcus* isolates, dextran (slime) characteristics may be examined by centrifugation, and the absence of a bacterial "pellet" following centrifugation indicates a dextran type slime. One of the aims of the present invention was the selection for *S. bovis* bacteria that did not produce dextran slime.

Typically, the vertebrate is a monogastric, herbivore or ruminant animal or human subject. Even more typically, the vertebrate is selected from the group consisting of human, non-human primate, murine, bovine, ovine, equine, porcine, caprine, leporine, avian, feline and canine. More typically, the vertebrate is selected from the group consisting of human, ovine, camelids, porcine, bovine, equine or canine.

Typically, the vaccine comprises live or dead intact cells of at least one of the microorganisms as defined in accordance with the first embodiment of the invention. More typically, the vaccine comprises cell lysate from at least one fermentative lactic acid producing microorganisms defined in the first embodiment of the invention. Even more typically, the vaccine comprises crude antigen mixture or purified antigen or antigens from at least one fermentative lactic acid producing microorganism defined in the first embodiment of the invention. Still more typically, the vaccine comprises outer membrane and associated proteins of at least one of the microorganisms defined in the first embodiment of the invention.

Typically, the fragment or fragments of the microorganism is present in the vaccine as an immunogenic polypeptide, glycopeptide or the like.

Typically, the vaccine comprises both live or dead intact cells of at least one of the microorganisms as defined in accordance with the first embodiment of the invention, together with outer membrane and associated proteins of at least one of these microorganisms, and/or a fragment(s) of at least one of these microorganism present as an immunogenic polypeptide, glycopeptide or the like.

Still more typically, the vaccine may be comprised of a combination of one of the following: live or dead intact cells of at least one of the microorganisms as defined in accordance with the first embodiment of the invention, outer membrane and associated proteins of at least one of these microorganisms, both dead intact cells of at least one of these microorganisms, together with outer membrane and associated proteins of at least one of the microorganisms of the invention, and/or a fragment(s) of the microorganism present as an immunogenic polypeptide, glycopeptide or the like, wherein the live or dead intact cells or outer membrane and associated proteins or immunogenic polypeptide, glycopeptide or the like, are derived from at least two microorganisms of the invention.

Typically, the vaccine is formulated for administration via intramuscular, subcutaneous, topical or other parenteral route. In general, the microorganisms of the present invention are commensal in nature, with a presence in the gut. Thus, oral administration is generally not an effective route of vaccination, and as a consequence, administration via an intramuscular, subcutaneous topical or other parenteral route is preferred.

Typically, the vaccine may also include cytokines, such as: G-CSF, GM-CSF, interleukins or tumour necrosis factor alpha, used singly or in combination.

Typically, the vaccine may comprise a combination of two or more of the microorganisms outlined in accordance with the first embodiment of the invention.

According to a second embodiment of the invention, there is provided a pharmaceutical composition for the prevention of lactic acidosis in a vertebrate comprising at least one isolated microorganism capable of producing lactic acid within the gut of a vertebrate, or fragment or fragments thereof, wherein said microorganism is selected from the group consisting of: *Clostridium*-like species, *Prevotella*-like species, *Bacteroides*-like species, *Enterococcus*-like species, *Selenomonas* species, non-dextran slime producing *Streptococcus* species and non-slime producing lactic acid bacterial isolates, together with a pharmaceutically acceptable carrier, adjuvants and/or diluent.

Typically, in the pharmaceutical composition of the present invention, the microorganism forms part of the normal gut flora or a vertebrate. More typically, the microorganism is involved in the aetiology of fermentative lactic acidosis in vertebrates. Still more typically, the microorganism is selected from the group consisting of: *Streptococcus equinus, Clostridium*-like *vitulinus, Selenomonas ruminantium, Prevotella*-like species, *Bacteroides*-like, *Enterococcus*-like species, *Streptococcus bovis* SbR1 and non-slime producing lactic acid bacterial isolates LAB02, LAB06 and LAB08. Yet still more typically, the microorganism is selected from the group consisting of: *Streptococcus bovis* (SbR1), *Streptococcus equinus* (SER1); *Streptococcus equinus* (SER2); *Selenomonas ruminantium* (SRR1); *Selenomonas ruminantium* (SRR3); *Clostridium*-like *vitulinus* (LVR3); *Clostridium*-like *vitulinus* (LVR4), *Prevotella*-like isolates LAB01 and LAB03, *Bacteroides*-like isolates LAB07 *Enterococcus*-like isolate LAB05, *Streptococcus bovis* SbR1, non-dextran slime producing *Streptococcus* isolate LAB04 and non-slime producing lactic acid bacterial isolates LAB02, LAB06 and LAB08.

More typically, the microorganism(s) within the pharmaceutical composition is selected from the group consisting of: *Streptococcus bovis* (SbR1) (NM99/04455), *Streptococcus equinus* (SER1) (NM99/04456); *Streptococcus equinus* (SER2) (NM99/04457); *Selenomonas ruminantium* (SRR1) (NM99/04458); *Selenomonas ruminantium* (SSR3) (NM99/04460); *Clostridium*-like *vitulinus* (LVR3) (NM99/04461); *Clostridium*-like *vitulinus* (LVR4) (NM99/04462), *Prevotella*-like isolates LAB01 (NM00/12630) and LAB03 (NM00/12632), *Bacteroides*-like isolates LAB07 (NM00/12636), *Enterococcus*-like isolate LAB05 (NM00/12634), *Streptococcus bovis* (SbR1), non-dextran slime producing *Streptococcus* isolate LAB04 (NM00/12633) and non-slime producing lactic acid bacterial isolates LAB02 (NM00/12631), LAB06 (NM00/12635) and LAB08 (NM00/12637).

Typically, the microorganism(s) within the pharmaceutical composition is provided as live cells, attenuated cells, killed whole cells, cell lysate, crude antigen mixture or purified antigen or antigen from the microorganism. More typically, the microorganism, and/or fragment or fragments thereof, is present in the pharmaceutical composition as outer membrane and associated proteins of the microorganism. Even more typically, the microorganism or glycopeptide, or the like. Yet still more typically, the pharmaceutical composition further comprises at least one cytokine, such as: G-CSF, GM-CSF, interleukin or tumor necrosis factor alpha, used singly or in combination.

Typically, the pharmaceutical composition may comprise a combination of two or more of the microorganisms defined the second embodiment of the invention.

Typically, the microorganism present in the pharmaceutical composition may exist as a monoculture of at least one microorganism defined in the second embodiment of the invention, or may be present as a mixed culture with other microorganisms, wherein the predominant microorganism(s) is that defined in the second embodiment of the invention.

Typically, the pharmaceutical composition in accordance with the second embodiment of the invention may also include an adjuvant. More typically, the adjuvant is selected from the group consisting of: Freunds Complete/Incomplete Adjuvant, Montenide Macrol Adjuvant, Phosphate Buffered Saline and Mannan oil emulsions, saponins (QuiLA) dextran (dextran sulphate, DEAE-Dextran), aluminum compounds (Imject Alum), N-acetylglucosamiyl-N-acetylmuramyl-L-alanyl-D-isoglutamine (Gerbu adjuvant). More typically, the adjuvant is selected from the group as described in the Vaccine 1995, vol 13, p 1203; 1993 vol 11 p 293; and 1992 vol 10 p 427, the disclosures of which are incorporated herein by reference.

2. Methods for Control of Acidosis

According to a third embodiment of the invention, there is provided a method for inducing an immune response against lactic acidosis in a vertebrate, said method comprising administering to said vertebrate an immunologically effective amount of the vaccine in accordance with the first embodiment of the invention, or a pharmaceutical composition in accordance with the second embodiment of the invention.

According to a fourth embodiment of the invention, there is provided the vaccine as defined in accordance with the first embodiment of the invention, or a pharmaceutical composition as defined in accordance with the second embodiment of the invention, when used in inducing an immune response against lactic acidosis in a vertebrate.

According to a fifth embodiment of the invention, there is provided the use of at least one isolated microorganism capable of producing lactic acid within the gut of a vertebrate, or fragment or fragments thereof, wherein said microorganism is selected from the group consisting of: *Clostridium*-like species, *Prevotella*-like species, *Bacteroides*-like species, *Enterococcus*-like species, *Selenomonas* species, non-dextran slime producing *Streptococcus* species and non-slime producing lactic acid bacterial isolates, or a pharmaceutical composition as defined in accordance with the second embodiment of the invention, in the preparation of a vaccine for the inducing an immune response against lactic acidosis in vertebrate.

Still more typically, the microorganism is selected from the group consisting of: *Streptococcus equinus*, *Clostridium*-like *vitulinus*, *Selenomonas ruminantium*, *Prevotella*-like species, *Bacteroides*-like species, *Enterococcus*-like species, *Streptococcus bovis* SbR1 and non-slime producing lactic acid bacterial isolates LAB02, LAB06 and LAB08. Yet still more typically, the microorganism is selected from the group consisting of: *Streptococcus bovis* (SbR1), *Streptococcus equinus* (SER1); *Streptococcus equinus* (SER2); *Selenomonas ruminantium* (SRR1); *Selenomonas ruminantium* (SSR3); *Clostridium*-like *vitulinus* (LVR3); *Clostridium*-like *vitulinus* (LVR4), *Prevotella*-like isolates LAB01 and LAB05, *Bacteroides*-like isolates LAB07, *Enterococcus*-like isolate LAB05, *Streptococcus bovis* SbR1, non-dextran slime producing *Streptococcus* isolate LAB04 and non-slime producing lactic acid bacterial isolates LAB02, LAB06 and LAB08.

Yet still more typically, the microorganism(s) is selected from the group consisting of: *Streptococcus bovis* (SbR1) (NM99/04455), *Streptococcus equinus* (SER1) (NM99/04456); *Streptococcus equinus* (SER2) (NM99/04457); *Selenomonas ruminantium* (SRR1) (NM99/04458); *Selenomonas ruminantium* (SRR3) (NM99/04460); *Clostridium*-like *vitulinus* (LVR3) (NM99/04461); *Clostridium*-like *vitulinus* (LVR4) (NM99/04462), *Prevotella*-like isolates LAB01 (NM00/12630) and LAB03 (NM00/12632), *Bacteroides*-like isolate LAB07 (NM00/12636), *Enterococcus*-like isolate LAB05 (NM00/12634), *Streptococcus bovis* (SbR1), non-dextran slime producing *Streptococcus* isolate LAB04 (NM00/12633) and non-slime producing lactic acid bacterial isolates LAB02 (NM00/12631), LAB06 (NM00/12635) and LAB08 (NM00/12637).

Typically, the vaccine or pharmaceutical composition administered in accordance with the third, fourth or fifth embodiments of the invention, may also be simultaneously or sequentially administered with cytokines, such as: G-CSF, GM-CSF, interleukins or tumour necrosis factor. Cytokines can also be combined with adjuvants to enhance the immune response.

According to a sixth embodiment of the invention, there is provided a method for the treatment and/or prophylaxis of lactic acidosis in a vertebrate in need of said treatment and/or prophylaxis, wherein said method comprises administering to said vertebrate a therapeutically effective amount of the vaccine in accordance with the first embodiment of the invention, or a pharmaceutical composition in accordance with the second embodiment of the invention.

According to a seventh embodiment of the invention, there is provided the vaccine as defined in accordance with the first embodiment of the invention, or the pharmaceutical composition as defined in accordance with the second embodiment of the invention, when used in the treatment and/or prophylaxis of lactic acidosis in a vertebrate in need of said treatment and/or prophylaxis.

According to an eighth embodiment of the invention, there is provided the use of at least one isolated microorganism capable of producing lactic acid within the gut of a vertebrate, or fragment or fragments thereof, wherein said microorganism is selected from the group consisting of: *Clostridium*-like species, *Prevotella*-like species, *Bacteroides*-like species, *Enterococcus*-like species, *Selenomonas* species, non-dextran slime producing *Streptococcus* species and non-slime producing lactic acid bacterial isolates, in the preparation of a medicament for the treatment and/or prophylaxis of disease in a vertebrate in need of said treatment and/or prophylaxis.

Typically, the microorganism(s) used in accordance with the eighth embodiment of the invention are selected from the group consisting of: *Streptococcus equinus*, *Clostridium*-like *vitulinus*, *Selenomonas ruminantium*, *Prevotella*-like species, *Bacteroides*-like species, *Enterococcus*-like species, *Streptococcus bovis* SbR1 and non-slime producing lactic acid bacterial isolates LAB02, LAB06 and LAB08. Even more typically, the microorganism is selected from the group consisting of: *Streptococcus bovis* (SbR1), *Streptococcus equinus* (SER1); *Streptococcus equinus* (SER2); *Selenomonas ruminantium* (SRR1); *Selenomonas ruminantium* (SRR3); *Clostridium*-like *vitulinus* (LVR3); *Clostridium*-like *vitulinus* (LVR4), *Prevotella*-like isolates LAB01 and LAB03, *Bacteroides*-like isolates LAB07, *Enterococcus*-like isolate LAB05, *Streptococcus bovis* SbR1, non-dextran slime producing *Streptococcus* isolate LAB04 and non-slime producing lactic acid beneath isolates LAB02, LAB06 and LAB08.

Yet still more typically, the microorganism(s) is selected from the group consisting of: *Streptococcus bovis* (SbR1) (NM99/04455), *Streptococcus equinus* (SER1) (NM99/04456); *Streptococcus equinus* (SER2) (NM99/04457); *Selenomonas ruminantium* (SSR1) (NM99/04458); *Selenomonas ruminantium* (SRR3) (NM99/04460); *Clostridium*-like *vitulinus* (LVR3) (NM 99/04461); *Clostridium*-like *vitulinus* (LVR4) (NM99/04462), *Prevotella*-like isolates LAB01 (NM00/12630) and LAB03 (NM00/12632), *Bacteroides*-like isolate LAB07 (NM00/12636). *Enterococcus*-like isolate LAB05 (NM00/12634), *Streptococcus bovis* (SbR1), non-dextran slime producing *Streptococcus* isolate LAB04 (NM00/12633) and non-slime producing lactic acid bacterial isolates LAB02 (NM00/12631). LAB06 (NM00/12635) and LAB08 (NM00/12637).

Typically, the method in accordance with the third or sixth embodiment of the invention, the vaccine of pharmaceutical composition in accordance with the fourth or seventh embodiment of the invention, or the use in accordance with the fifth or eighth embodiment of the invention, further comprises administering at least one cytokine, such as: G-CSF, GM-CSF, interleukins or tumour necrosis factor.

Typically, the method in accordance with the third or sixth embodiments of the invention, the variance or pharmaceutical composition in accordance with the fourth or seventh embodiment of the invention, or the use in accordance with the fifth or eighth embodiment of the invention, further comprises administering an active agent to the vertebrate to assist in the treatment and/or prophylaxis of lactic acidosis in the vertebrate in need of said treatment and/or prophylaxis.

Typically, in the method in accordance with the third or sixth embodiment of the invention, the vaccine or pharmaceutical composition in accordance with the fourth or seventh embodiment of the invention, or the use in accordance with the fifth or eighth embodiment of the invention, the active agent is selected from the group consisting of: antibiotics, enzyme preparations, clay preparations, compounds which slow the digesta flow, prebiotics and probiotics.

According to a ninth embodiment of the invention, there is provided a method for the treatment and/or prophylaxis of lactic acidosis in a vertebrate in need of said treatment and/or prophylaxis, wherein said method comprises administering to said vertebrate a therapeutically effective amount of an active agent capable of preventing or controlling lactic acid accumulation in the gut of a vertebrate, and wherein said lactic acid is produced by at least one microorganism selected from the group consisting of: *Clostridium*-like species, *Prevotella*-like species, *Bacteroides*-like species, *Enterococcus*-like species, *Selenomonas* species, non-dextran slime producing *Streptococcus* species and non-slime producing lactic acid bacterial isolates.

According to a tenth embodiment of the invention, there is provided an active agent capable of preventing or controlling lactic acid accumulation in the gut of a vertebrate, when used in the treatment and/or prophylaxis of lactic acidosis in a vertebrate in need of said treatment and/or prophylaxis, wherein said lactic acid is produced by at least one of the isolated microorganisms selected from the group consisting of: *Clostridium*-like species, *Prevotella*-like species, *Bacteroides*-like species, *Enterococcus*-like species, *Selenomonas* species, non-dextran slime producing *Streptococcus* species and non-slime producing lactic acid bacterial isolates.

According to an eleventh embodiment of the invention, there is provided use of an active agent capable of preventing or controlling lactic acid accumulation in the gut of a vertebrate, in the preparation of a medicament for the treatment and/or prophylaxis of lactic acidosis in a vertebrate in need of said treatment and/or prophylaxis, wherein said lactic acid is produced by at least one of the isolated microorganisms selected from the group consisting of: *Clostridium*-like species, *Prevotella*-like species, *Bacteroides*-like species, *Enterococcus*-like species, *Selenomonas* species, non-dextran slime producing *Streptococcus* species and non-slime producing lactic acid bacterial isolates.

Typically, in the method, active agent or use in accordance with the ninth, tenth or eleventh embodiments of the invention, the microorganism is selected from the group consisting of: *Streptococcus equinus*, *Clostridium*-like *vitulinus*, *Selenomonas ruminantium*, *Prevotella*-like species, *Bacteroides*-like species, *Enterococcus*-like species, *Streptococcus bovis* SbR1 and non-slime producing lactic acid bacterial isolates LAB02, LAB06 and LAB08. Even more typically, the microorganism is selected from the group consisting of: *Streptococcus bovis* (SbR1), *Streptococcus equinus* (SER1); *Streptococcus equinus* (SER2); *Selenomonas ruminantium* (SRR1); *Selenomonas ruminantium* (SRR3); *Clostridium*-like *vitulinus* (LVR3); *Clostridium*-like *vitulinus* (LVR4), *Prevatella*-like isolates LAB01 and LAB03, *Bacteroides*-like isolates LAB07, *Enterococcus*-like isolate LAB05, *Streptococcus bovis* SbR1, non-dextran slime producing *Streptococcus* isolate LAB04 and non-slime producing lactic acid bacterial isolates LAB02, LAB06 and LAB08.

Yet still more typically, the microorganism(s) is selected from the group consisting of: *Streptococcus bovis* (SbR1) (NM99/04455), *Streptococcus equinus* (SER1) (NM99/04456); *Streptococcus equinus* (SER2) (NM99/04457); *Selenomonas ruminantium* (SRR1) (NM99/04458); *Selenomonas ruminantium* (SRR3) (NM99/04460); *Clostridium*-like *vitulinus* (LVR3) (NM99/04461); *Clostridium*-like *vitu-*

*linus* (LVR4) (NM99/04462), *Prevotella*-like isolates LAB01 (NM00/12630) and LAB03 (NM00/12632), *Bacteroides*-like isolate LAB07 (NM00/12636), *Enterococcus*-like isolate LAB05 (NM00/12634), *Streptococcus bovis* (SbR1), non-dextran slime producing *Streptococcus* isolate LAB094 (NM00/12633) and non-slime producing lactic acid bacterial isolates LAB02 (NM00/12631), LAB06 (NM00/12635) and LAB08 (NM00/12637).

Typically, in the method, active agent or use in accordance with the ninth, tenth or eleventh embodiments of the invention, the active agent is used in conjunction with a vaccine according to the first or seventeenth embodiment of the invention.

Typically, in the method, active agent or use in accordance with the ninth, tenth or eleventh embodiments of the invention, the active agent is selected from the group consisting of: antibiotics, enzyme preparations, clay preparations, compounds which slow the digestion flow, prebiotics and probiotics.

The following relates to any one of the third through to eleventh embodiments of the invention.

Typically, the antibiotic is active against gram-positive lactic acid producing microorganisms.

Typically, the enzyme preparation is active against lactic acid producing gram-negative bacteria.

Typically, the clay preparation is active against lactic acid producing Gram-negative or Gram positive bacteria.

Typically, the compounds which slow digesta flow rate are indirectly active against lactic acid producing gram-negative bacteria. More typically, the compounds which slow digesta flow rate are typically selected from the group consisting of biologically active peptides (BAP), compounds active on the automatic nervous system. 5HT agonists/antagonists, motilin antagonists, NO promoters, and dopamine.

Typically, the probiotic preparation include bacteria selected from the group consisting of: *Megasphera, Veillenolla, Selenomonas, Propionibacterium, Anaerovibro* and *Peptococcus*. More typically, the probiotic preparations include yeast and mycelial preparations capable of utilising lactic acid, and converting lactic acid to volatile fatty acids and other end products.

Typically, the active agent is active against at least one of the isolated microorganisms as defined in accordance with the first embodiment of the invention.

Typically, the antibiotic is an antibiotic active against lactic acid producing bacteria that can be selected from any listing of antibiotic compounds such as available in text books, and reports such as the Report of the Joint Expert Advisory Committee on Antibiotic Resistance (JETACAR, 1999), the disclosure of which is incorporated herein by reference.

More typically, the antibiotic is selected from the group consisting of: Acyclovir (Zovirax), Amantadine (Symmetrel), Amikacin )generic), Gentamicin (generic), Tobramycin (generic), Amoxicillin (generic), Amoxicillin/Clavulanate (Augmentin), Amphoetericin B (Fungizone), Ampicillin (generic), Atovaquon (Mepron), Cefazolin (generic), Cefepime (Maxipime), Cefotaxime (Claforan), Cefuroxime (Zinacef), Chloramphienicol (generic), Clotrimazole (Mycelex), Ciprofloxacin (Cipro), Clarithromycin (Biaxin), Dicloxacillin (generic), Doxycycline (generic), Erythromycin lactobionate and other salts Fluconazole (Diflucan), F scarnet (Foscavir), Ganciclovir, (Cytovene, DHPG), Imipenem/Cilastatin (Primaxin), Ketoconazole (generic), Metronidazole (Flagyl), Nitrofurantoin Nystatin (generic) fluconazole, or amphotericin, Penicillin T (generic) (sodium or potassium salt), Pentamidine (generic), Piperazillin/Tazobactam (Zosyn), Rifampin (Rifadin), Ticarcillin/Clavulanate (timentin), Trimethoprin Sulfamethoxazole, Vancomycin (generic), and any combination thereof.

More typically, the antibiotics may be used in combination with any antibiotic agents active against lactic acid producing bacteria such as *Streptococcus* spp. *Clostridium*-like and *Lactobacillus* spp. Still more typically, the antibiotic agents active against gram-positive lactic acid producing bacteria may be selected from the group consisting of: glycopeptide antibiotics, more typically, ardacin, avoparcin, telcoplanin or vancomycin; glycolipid antibiotics, more typically flavomycin (bambermycin); Streptogramin antibiotics, more typically virginiamycin; polypeptide antibiotics, more typically bacitracin zinc, bacitracin methylene disalicylate, virginiamycin S or polymixins (B & E); macrolide antibiotics, more typically tylosin, spiramycin, virginiamycin M. josamycin, spectinomycin or erythromycin; or sulfur-containing peptide antibiotics, more typically thiopeptone, thiopeptin, sulfomycin, thiostrepton, sporangiomycin, siomycin or taitomycin; lincosamide antibiotics, more typically lincomycin or clindamycin; or pleuromutilins tiamulin; or nitrofuran antibiotics, more typically nitrofurantoin, nitrofurazone or furazolidone; tetracycline antibiotics, more typically clortetracycline or oxytetracycline; doxycycline, minocycline, penicillin antibiotics, more typically penicillinase-resistant penicillins, such as oxacillin or methicillin, penicillin V or amplicillin; polythiazole antibodies, more typically nosiheptide; or ionophore antibiotics, more typically lasalocid, tetronasin, naracin or salinomycin; or, novoiocin sodium, bottromycin tartrate; streptogramin antibiotics, more typically, quinupristin/dalfopristin (RP 59500; Syneroid) or streptogramin combinations [quinupristidn/dalfopristin (RP 59500; Syneroid)], everninomycin derivatives (SCH 27899), oxazolidinones (U-100572, U-100766), fluoroquinolone antibiotics, more typically, ciprofloxacin, oxfloxacin, clinafloxacin, DU 6859a, grepafloxacin, levofloxacin, sparfloxacin or eprofloxacin, trovafloxacin; beta-lactam antibiotics; nitrovin (payzone), enramycin, mupiricin, magainin antibiotics, chloramphenicols and related compounds, including fluorphenicol thiamphenicol, and any combination thereof.

Typically, the antibiotics active agent against lactic acid producing miroorganisms may be used in combination with the vaccine in accordance with the first or seventeenth embodiments of the invention.

Typically, the antibiotics active against gram-positive lactic acid producing microorganisms may be used in conjunction with the vaccine in accordance with the first or seventh embodiments of the invention. For example animals may be immunised against *Selenomonas* type bacteria and fed diets containing the antibiotic virginiamycin active against *Streptococcus* spp. and lactobacilli of lactic acid producing bacteria.

Typically, vaccines against Gram positive lactic acid producing bacteria can be used in combination with the vaccine in accordance, with the first or seventeenth embodiments of the invention. For example, animals may be immunised against the Gram negative *Selenomonas* type bacteria and against *Streptococcus* spp. and *Clostridium*-like lactic acid producing bacteria.

Typically, vaccines against Gram positive lactic acid producing bacteria may also be used in combination with vaccines against Gram negative lactic acid producing bacteria, and these vaccines can also be used in conjunction with antibiotic compounds active against lactic acid bacteria.

Typically, the enzyme preparation is active against lactic acid producing gram-negative bacteria. More typically, enzyme preparations are designed to reduce the passage of fermentable carbohydrate to the hind gut through improving the digestion and absorption in the intestine of starches, disaccharides, oligosaccharides, non-starch polysaccharides, protein starch complexes and any polysaacharide which is incompletely digested in the intestine, but which is readily fermentable in the hind gut.

Typically, preferred enzymes for the break down of non-starch polysaccharides and starches include the following: glyconases including: amylase, maltase, invertase, α-glucosidases, emulsin, and amyloglucosidase; β-glucanases β-glucanase, xylanase; enzymes which break down galactosides of the raffinosse series and other α-galactosides including α-galactosidase, enzymes which break down the proteins forming part of the matrix surrounding starches, sugars and non-starch carbohydrates in plant material, including: pepsin, trypsin, trypsinogen, chymotrypsin and natural and synthetic porteolytic enzymes of chemical or microbial origin, enzymes which depolymerise non-starch polysaccharides including: arabinoxylans and β-glucans, and enzymes active in the break down of cellulose, including: cellulase, enzymes active in the break down of colloidal polysaccharides, pectic substances, which include: galactouronans, galactan and arabinans, as well as the neutral polysaccharides such as xyloglucans and galactomannans and other non-starch polysaccharides such as: rhamnogalacturonan with arabinose and galactose, arabinogalactan, glucan, xyloglucan, galactouronan with arabinose and uronan with arabinose. These enzymes can be used individually or in combination.

Typically, the enzyme preparation active against lactic acid accumulation from gram-negative lactic acid producing microorganisms may be used in conjunction with the vaccine in accordance with the first or seventeenth embodiments of the invention.

Typically, the clay preparation is active against lactic acid producing Gram-negative or Gram positive bacteria. More typically, clay preparations are designed to reduce the rate of fermentation and binds specific ions in a way which reduces the adverse effects of rapid fermentation of starch and other soluble carbohydrates in the gastrointestinal tract.

Typically, preferred clays for reducing the rate of fermentation and the osmotic effects of rapid fermentation within the gut include: kaolinite, bentonite, montmorrilonite, illite, clinolipolite, heulandite, palygorsite, saponite, smectite, chrysotile, lizaridite, talc, pyrophhyllite, vermiculite, beidellite, halloysite or zeolite types of clay, and these can be activated by a wide range of ions including sodium, calcium, potassium and mixtures of these and other ions. These clays can be used individually or in combination.

Typically, the clay preparation active against lactic acid accumulation from gram-negative lactic acid producing microorganisms may be used in conjunction with the vaccine in accordance with the first or seventeenth embodiments of the invention.

Typically, the compounds which slow digesta flow rate are indirectly active against lactic acid producing gram-negative bacteria. More typically, by administering compounds which slow digesta flow rate, intestinal digestion and absorption are increased, reducing the amount of fermentable substrate passing to the hind gut.

Generally, preferred agents to slow the flow of digestion include biologically active peptides (BAP) in a form which will reach the duodenum, and are active in modulating the activity of the digestive track, gastric emptying and the rate of passage through the intestine. More typically, these biologically active peptides include opioid peptides. Compounds active on the autonomic nervous system (eg atropine and atropine-like compounds) may affect digesta flow and have similar effects. Compounds such as 5HT agonists/antagonists, motilin antagonists, NO promoters, dopamine agonists may also be used.

Whilst a range of proteins potentially produce opioid peptides on hydrolisation, the β-casomorphins, which can be derived from β-casein increasing casein during β-casein digestion, and particularly active.

Even more typically, the biologically active peptides include cholecystokinin (CCK), the M1 fraction of virginiamycin and the analogue of virginiamycin fraction M1 compound L-156. These biologically active peptides can be used individually or in combination.

It has traditionally been assumed that the nutritional benefits of proteins are only related to the essential amino acids supplied to the animal during digestion and absorption. However through the supply of biologically active peptides and the production of naturally occurring opioid peptides, the rate of digesta passage is reduced and this results in more efficient intestinal digestion and less fermentable substrate passing to the hind gut which can contribute to acidic gut syndrome.

Practical methods of supplying biologically active opioid peptides is through dietary supplementation with proteins such as casein and blood meal. For ruminant animals the best results are obtained through protection of the protein against rumen degradation by polymer coating technology, slow-release capsules, or through formaldehyde treatment.

Typically, the compounds which slow digesta rate and thereby active against lactic acid accumulation from gram-negative lactic acid producing microorganisms may be used in conjunction with the vaccine in accordance with the first or seventeenth embodiment of the invention.

Typically, probiotic agents are also active against lactic acid producing gram-negative bacteria. More typically, the probiotic reduces lactic acid accumulation from at least one of the microorganisms as defined in accordance with the first embodiment of the invention by: formation of alternative end products of fermentation; through increased utilisation of lactic acid; or through the conversion of lactic acid to volatile fatty acids which can be absorbed from the gut, thereby reducing acidity in the gut.

The effects of immunisation and antibiotic use can be further enhanced by their use in combination with probiotics in the form of bacteria selected for favourable fermentation characteristics. For example, *Megasphera elsdenii* and certain strains of *Selenomonas ruminantium* that can ferment sugars or starch without accumulation of lactic acid may be used in a probiotic composition. Other probiotic bacteria specifically selected for reducing lactic build up during starch fermentation include Lu-12 SU109 and SuIII (Aihua Liu, 1999 see p117). Strains of *Selenomonas ruminantium* vary significantly in their ability to ferment starch and in their ability to utilise lactic acid. While some strains have been isolated for their ability to utilise lactic acid, the strains (SRR1 and SRR3) disclosed in the present invention are aggressive producers of lactic acid. This combination of immunisation/antibiotic treatment with the use of probiotics allows the control of lactic acid producing bacteria and thus allowing the better establishment of favourable starch utilising organisms. The effect of this combination of treatments is synergistic and not merely additive.

Typically, preferred probiotic preparations include bacteria which ferment starch and sugars to end products other than lactic acid, (ie volatile fatty acids), and bacteria which convert lactic acid to volatile fatty acids. More typically, microorganisms such as *Megasphera elsdentiii* and certain strains of *Selenomonas ruminantium* can ferment sugars or starch without accumulation of lactic acid and these strains can be used to reduce lactic acid accumulation.

More typically, the probiotic preparations may include bacteria that belong to the genera: *Succinomonas, Butyrivibrio, Bacteroides* and *Succinivibrio*. These bacteria can be used individually or in combinations. More typically, the probiotic preparations may include anaerobic bacteria. Even more typically, the probiotic preparations may include bacteria selected from the group consisting of: *Megasphera, Veillenolla, Selenomonas, Propionibacterium, Anaerovibrio* and *Peptococcus*. These bacteria can be used individually or in combinations. Still more typically, preferred probiotic preparations include yeast and mycelial preparations capable of utilising lactic acid, and converting lactic acid to volatile fatty acids and other end products. Yet still more typically, the probiotic preparations may include yeast and mycelial preparations such as Yea-Sacc.

Typically, at least any two of the above sample microorganisms of the probiotic preparation may be used in combination in the probiotic preparation.

Typically, the above probiotics may be used in conjunction with the vaccine in accordance with the first or seventeenth embodiments of the invention.

Typically, a combination of immunisation/active agent treatment, allows the control harmful lactic acid producing bacteria and thus allowing the better establishment of favourable starch utilising organisms. The effect of this combination of treatment is synergistic and not merely additive.

Typically, lactic acidosis is associated with a wide range of disorders, including: immune disorders, including diabetes, dermatitis, arthritis, rheumatoid arthritis, multiple sclerosis, amyotrophic lateral sclerosis, chronic fatigue syndrome, myasthenia gravis, inflammatory bowel disease, coeliac disease, irritable bowel syndrome, crohn's disease, effects on the pancreas, kidneys, thryoid and other organs of the endocrine system, and immune conditions associated with localised inflammation of sections of the gut; homeostasis disorders, including mineral and electrolyte imbalances, such as osteoporosis; impaired reproductive performance; predisposition to ulceration of the gastrointestinal tract; respiratory tract disorders, including asthma; attention deficit disorder, autism, atopy, hypertension; infected gums and dental caries; viral infections, including herpes; predisposition to infection by bacteria, viruses and mycoplasma fungi or protozoa; exacerbation of heat stress, and impaired hair, milk production and wool growth.

3. Nucleic acid molecules and antibodies

According to a twelfth embodiment of the invention, there is provided an isolated nucleic acid molecule comprising a polynucleotide sequence capable of selectively hybridising to at least a portion of the nucleic acid of at least one of the isolated microorganisms selected from the group consisting of: *Clostridium*-like species, *Prevotella*-like species, *Bacteroides*-like species, *Enterococcus*-like species, *Selenomonas* species, non-dextran slime producing *Streptococcus* species and non-slime producing lactic acid bacterial isolates.

Typically, the microorganism is selected from the group consisting of: *Streptococcus equinus, Clostridium*-like *vitulinus, Selenomonas ruminantium, Prevotella*-like species, *Bacteroides*-like species, *Enterococcus*-like species, *Streptococcus bovis* SbR1 and non-slime producing lactic acid bacterial isolates LAB02, LAB06 and LAB08. Even more typically, the microorganism is selected from the group consisting of: *Streptococcus bovis* (SbR1), *Streptococcus equinus* (SER1); *Streptococcus equinus* (SER2); *Selenomonas ruminantium* (SRR1); *Selenomonas ruminantium* (SRR3); *Clostridium*-like *vitulinus* (LVR3); *Clostridium*-like *vitulinus* (LVR4), *Prevotella*-like isolates LAB01 and LAB03, *Bacteroides*-like isolates LAB07, *Enterococcus*-like isolate LAB05, *Streptococcus bovis* SbR1, non-dextran slime producing *Streptococcus* isolate LAB04 and non-slime producing lactic acid bacterial isolates LAB02, LAB06 and LAB08.

Yet still more typically, the microorganism is selected from the group consisting of: *Streptococcus bovis* (SbR1) (NM99/04455), *Streptococcus equinus* (SER1) (NM999/04456); *Streptococcus equinus* (SER2) (NM99/04457); *Selenomonas ruminantium* (SRR1) (NM99/04458); *Selenomonas ruminantium* (SRR3) (NM99/04460); *Clostridium*-like *vitulinus* (LVR3) (NM99/4461); *Clostridium*-like *vitulinus* (LVR4) (NM99/04462), *Prevotella*-like isolates LAB01 (NM00/12630) and LAB03 (NM00/12632), *Bacteroides*-like isolates LAB07 (NM00/12636), *Enterococcus*-like isolates LAB05 (NM00/12634), *Streptococcus bovis* (SbR1), non-dextran slime producing *Streptococcus* isolate LAB04 (NM00/12633) and non-slime producing lactic acid bacterial isolates LAB02 (NM00/12631), LAB06 (NM00/12635) and LAB08 (NM00/12637).

According to a thirteenth embodiment of the invention, there is provided an isolated nucleic acid molecule comprising a polynucleotide sequence selected from the group consisting of: SEQ ID Nos: 1–7.

Typically, the nucleic acid molecule corresponds to a DNA or RNA molecule.

Typically, the nucleic acid molecule also includes within its scope an analogue of the polynucleotide sequence defined in accordance with the twelfth or thirteenth embodiments of the invention, wherein said analogue encodes a polypeptide having a biological activity which is functionally the same as the polypeptide(s) encoded by the polynucleotide sequence defined in accordance with the twelfth or thirteenth embodiments of the invention, wherein said polynucleotide sequence can be located and isolated using standard techniques in molecular biology, without undue trial and experimentation.

Typically, the nucleic acid molecule also includes within its scope an analogue of the polynucleotide sequence defined in accordance with the twelfth or thirteenth embodiments of the invention, which has at least 45% homology to the polynucleotide sequences so defined. More typically, the analogue of the polynucleotide sequences has at least 55% homology, still more typically the analogue has at least 60% homology, even more typically, the analogue has at least 75% homology, still more typically, the analogue has at least 85% homology, and yet still more typically, the analogue has at least 90% homology, and yet even still more typically, the analogue has at least 95–99% homology to the polynucleotide sequences so defined.

The degree of homology between two nucleic acid sequences may be determined by means of computer programs known in the art such as GAP provided in the GCG program package (Program Manual for the Wisconsin Package, Version 8, August 1996, Genetics Computer Group, 575 Science Drive, Madison, Wis., USA 53711) (Needleman, S. B. and Wunsch, C. D., (1970), Journal of Molecular Biology, 48, 443–453). Using GAP with the following settings for DNA sequence comparison: GAP creation penalty of 5.0 and GAP extension penalty of 0.3.

Typically, the nucleic acid molecule also includes within its scope an analogue of the polynucleotide sequence defined in accordance with the twelfth or thirteenth embodiments of the invention, wherein said analogue is capable of hybridising to the polynucleotide sequences defined in accordance with the twelfth or thirteenth embodiments of the invention under conditions of low stringency. More typically, low stringency hybridisation conditions correspond to hybridisation performed in conditions of low temperature and/or high salt. Even more typically, low stringency hybridisation conditions correspond to hybridisation performed at 50° C. in 6×SSC.

For example, suitable experimental conditions for determining whether a given nucleic acid molecule, hybridises to a specified nucleic acid may involve following the following hybridisation routine: presoaking of a filter containing a relevant sample of the nucleic acid to be examined in 5× SSC for 10 min, and prehybridisation of the filter in a solution of 5× SSC, 5× Denhardt's solution, 0.5% SDS and 100 µg/ml of denatured sonicated salmon sperm DNA, followed by hybridisation in the same solution containing a concentration of 10 ng/ml of a $^{32}$P-dCTP-labeled probe for 12 hours at approximately 45° C., in accordance with the hybridisation methods as described in Sambrook et al. (1989; Molecular Cloning, A Laboratory Manual, 2nd edition, Cold Spring Harbor, N.Y.).

The filter is then washed twice for 30 minutes in 2× SSC, 0.5% SDS at least 55° C. (low stringency), at least 60° C. (medium stringency), at least 65° C. (medium/high stringency), at least 70° C. (high stringency), or at least 75° C. (very high stringency). Hybridisation may be detected by exposure of the filter to an X-ray film.

Further, there are many conditions and factors, well known to those skilled in the art, which may be used to alter the stringency of hybridisation. For instance, alterations to features such as: the length and nature (DNA, RNA, base composition) of the nucleic acid to be hybridised to a specified nucleic acid; concentration of salts and other components, such as the presence or absence of formamide, dextran sulfate, polyethylene glycol etc; and altering the temperature of the hybridisation and/or washing steps, all influence the dynamics and stringency of nucleic acid hybridisation.

Further, it is also possible to theoretically predict whether or not two given nucleic acid sequences will hybridise under certain specified conditions. Accordingly, as an alternative to the empirical method described above, the determination as to whether an analogous nucleic acid sequence will hybridise to the nucleic acid molecule in accordance with the twelfth or thirteenth embodiments of the invention, can be based on a theoretical calculation of the $T_m$ (melting temperature) at which heterologous nucleic acid sequences with known sequences will hybridise under specified conditions, such as salt concentration and temperature.

In determining the melting temperature for heterologous nucleic acid sequences ($T_{m(hetero)}$) it is necessary first to determine the melting temperature ($T_{m(homo)}$) for homologous nucleic acid sequence. The melting temperature ($T_{m(homo)}$) between two fully complementary nucleic acid strands (homoduplex formation) may be determined in accordance with the following formula, as outlined in Current Protocols in Molecular Biology, John Wiley & Sons, 1995, as:

$$T_{m(homo)} = 81.5° C. + 16.6(\log M) + 0.41 (\%GC) - 0.61 (\% form) - 500 mL$$

M=denotes the molarity of monovalent cations,
%GC=% guanine (G) and cytosine (C) of total number of bases in the sequence,
% form=% formamide in the hybridisation buffer, and
L=the length of the nucleic acid sequence.

$T_m$ determined by the above formula is the $T_m$ of a homoduplex formation ($T_{m(homo)}$) between two fully complementary nucleic acid sequences. In order to adapt the $T_m$ value to that of two heterologous nucleic acid sequences, it is assumed that a 1% difference in nucleotide sequence between two heterologous sequences equals a 1° C. decrease in $T_m$. Therefore, the $T_{m(hetero)}$ for the heteroduplex formation is obtained through subtracting the homology % difference between the analogous sequence in question and the nucleotide probe described above from the $T_{m(homo)}$.

Typically the nucleic acid molecule in accordance with the twelfth or thirteenth embodiments of the invention also includes within its scope a nucleic acid molecule which is an oligonucleotide fragment of these polynucleotide sequences.

Typically, the oligonucleotide fragment is between about 10 to about 100 nucleotides in length. More particularly, the oligonucleotide fragment is a between about 10 to about 75 nucleotides in length. Even more typically, the oligonucleotide fragment is between about 15 to about 50 nucleotides in length. Even more typically still, the oligonucleotide fragment is between about 15 to about 30 nucleotides in length. Yet still more typically, the oligonucleotide fragment is between about 5 to about 25 nucleotides in length.

According to a fourteenth embodiment of the invention, there is provided a vector comprising the nucleic acid molecule in accordance with the twelfth or thirteenth embodiments of the invention.

Typically, the vector is a shuttle or expression vector. More typically, the vector is selected from the group consisting of: viral, plasmid, bacteriophage, phagemid, cosmid, bacterial artificial chromosome, and yeast artificial chromsome. More typically, the vector is a plasmid and may be selected from the group consisting of: pBR322, M13mp18, pUC18 and pUC19. Even more typically, the vector is a bacteriophage and may be selected from λgt10 and λgt11 or phage display vectors.

According to a fifteenth embodiment of the invention, there is provided a host cell transformed with the vector in accordance with the fourteenth embodiment of the invention.

Typically, the host cells are procaryotic or eucaryotic in nature. More typically, the procaryotic host cells include bacteria, and examples of such bacteria include: *E. coli, Bacillus, Streptomyces, Pseudomonoas, Salmonella,* and *Serraria*.

More typically, the eucaryotic host cells may be selected from the group consisting of: yeast, fungal, plant, insect cells and mammalian cells, either in vivo or in tissue culture. Examples of mammalian cells include: CHO cell lines, COS cell lines, HeLa cells, L cells, murine 3T3 cells, c6 glioma cells and myeloma cell lines.

According to a sixteenth embodiment of the invention, there is provided an antibody raised against at least one lactic acid producing microorganism, wherein said microorganism is selected from the group consisting of: *Clostridium*-like species, *Prevotella*-like species, *Bacteroides*-like species, *Enterococcus*-like species, *Selenomonas* species, non-dextran slime producing *Streptococcus* species and non-slime producing lactic acid bacterial isolates.

Typically, the microorganism is selected from the group consisting of: *Streptococcus equinus, Clostridium*-like *vitulinus, Selenomonas ruminantium, Pravotella*-like species,

*Bacteroides*-like species, *Enterococcus*-like species, *Streptococcus bovis* SbR1 and non-slime producing lactic acid bacterial isolates LAB02, LAB06 and LAB08. Even more typically, the microorganism is selected from the group consisting of: *Streptococcus bovis* (SbR1), *Streptococcus equinus* (SER1); *Streptococcus equinus* (SER2); *Selenomonas ruminantium* (SRR1); *Selenomonas ruminantium* (SRR3); *Clostridium*-like *vitulinus* (LVR3); *Clostridium*-like *vitulinus* (LVR4), *Prevotella*-like isolates LAB01 and LAB03, *Bacteroides*-like isolates LAB07, *Enterococcus*-like isolate LAB05, *Streptococcus bovis* SbR1, non-dextran slime producing *Streptococcus* isolate LAB04 and non-slime producing lactic acid bacterial isolates LAB02 LAB 06 and LAB08.

Yet still more typically, the microorganism(s) is selected from the group consisting of: *Streptococcus bovis* (SbR1) (NM99/04455), *Streptococcus equinus* (SER1) (NM99/04456): *Streptococcus equinus* (SER2) (NM99/04457); *Selenomonas ruminantium* (SRR1) (NM99/04458); *Selenomonas ruminantium* (SRR3) (NM99/04460); *Clostridium*-like *vitulinus* (LVR3) (NM99/04461); *Clostridium*-like *vitulinus* (LVR4) (NM99/04462), *Prevotella*-like isolates LAB01 (NM00/12630) and LAB03 (NM00/12632), *Bacteroides*-like LAB07 (NM00/12636), *Enterococcus*-like isolate LAB05 (NM00/12634), *Streptococcus bovis* (SbR1), non-dextran slime producing *Streptococcus* isolate LAB04 (NM00/12633) and non-slime producing lactic acid bacterial isolates LAB02 (NM00/12631), LAB06 (NM00/12635) and LAB08 (NM00/12637).

Typically, the antibody in accordance with the sixteenth embodiment of the invention is raised against at least one of the following:
(a) at least one fermentative lactic acid producing microorganism as defined in the sixteenth embodiment of the invention;
(b) intact cells of least one fermentative lactic acid producing microorganism as defined in the sixteenth embodiment of the invention;
(c) cell lysate from at least one fermentative lactic acid producing microorganism as defined in the sixteen embodiment of the invention;
(d) crude antigen mixture or purified antigen or antigens from at least one fermentative lactic acid producing microorganism as defined in the sixteenth embodiment of the invention;
(e) outer membrane and associated proteins of at least one fermentative lactic acid producing microorganism as defined in the sixteenth embodiment of the invention.

Typically, the antibodies in accordance with the sixteenth embodiment may be present in a composition further comprising antibodies raised against at least one of the following:
(f) at least one fermentative lactic acid producing strain selected from *Streptococcus bovis* or lactobacilli;
(g) intact cells of at least one fermentative lactic acid producing strain selected from *Streptococcus bovis* or lactobacilli;
(h) cell lysate from at least one fermentative lactic acid producing strain selected from *Streptococcus bovis* or lactobacilli;
(i) crude antigen mixture or purified antigen or antigens from at least one fermentative lactic acid producing strain selected from *Streptococcus bovis* or lactobacilli;
(j) outer membrane and associated proteins of at least one fermentative lactic acid producing strain selected from *Streptococcus bovis* or lactobacilli.

More typically, the antibodies in accordance with the sixteenth embodiment may be present in a composition further comprising antibodies raised against at least one of the following:
(k) *Streptococcus bovis* (strain Sb-5) deposited with the Australian Government N94/8255;
(l) intact cells of *Streptococcus bovis* (strain Sb-5) deposited with the Australian Government Analytical Laboratories (AGAL) on 8 Mar. 1994, and given accession number N94/8255;
(m) cell lysate from *Streptococcus bovis* (strain Sb-5) deposited with the Australian Government Analytical Laboratories (AGAL) on 8 Mar. 1994, and given accession number N94/8255;
(n) crude antigen mixture or purified antigen or antigen from *Streptococcus bovis* (strain Sb-5) deposited with the Australian Government Analytical Laboratories (AGAL) on 8 Mar. 1994, and given accession number N94/8255;
(o) outer membrane and associated proteins of *Streptococcus bovis* (strain Sb-5) deposited with the Australian Government Analytical Laboratories (AGAL) on 8 Mar. 1994, and given accession number N94/8255.

Typically, the antibodies in accordance with the sixteenth embodiment of the invention can be comprised of a polyclonal mixture, or may be monoclonal in nature. Further, antibodies can be entire immunoglobulins derived from natural sources, or from recombinant sources. The antibodies of the present invention may exist in a variety of forms, including for example as a whole antibody, or as an antibody fragment, or other immunologically active fragment thereof, such as complementarity determining regions.

The antibody (or fragment thereof) in accordance with the sixteenth embodiment of the present invention has binding affinity to a microorganisms capable of producing acid in the gut of vertebrates in vertebrates. Preferably, the antibody (or fragment thereof) has binding affinity or avidity greater than about $10^5$ $M^{-1}$, more preferably greater than about $10^6$ $M^{-1}$, more preferably still greater than about $10^7$ $M^{-1}$ and most preferably greater than about $10^8$ $M^{-1}$.

The techniques for generating and reviewing binding affinity are reviewed in Scatchard (1949). Annals of the New York Academy of Sciences, 51, 660–672, and Munson (1983). Methods in Enzymology 92, 543–577, the contents of each of which are incorporated herein by reference.

According to a seventeenth embodiment of the invention, there is provided a vaccine comprising at least one of the antibodies in accordance with the sixteenth embodiment of the invention together with a pharmaceutically acceptable carrier, adjuvant and/or diluent.

4. Diagnostic of Acidosis

According to an eighteenth embodiment of the invention, there is provided a diagnostic kit for the detection of microorganisms having a role in lactic acidosis in a vertebrate, said kit comprising at least one of the antibodies in accordance with the sixteenth embodiment of the invention, together with a diagnostically acceptable carrier and/or diluent.

Typically, the diagnostic kit may also contain antibodies capable of detecting at least one lactic acid producing strain selected from: *Clostridium*-like species, *Prevotella*-like species, *Bacteroides*-like species, *Enterococcus*-like species, *Selenomonas* species, non-dextran slime producing *Streptococcus* species and non-slime producing lactic acid bacterial isolates.

Typically, the kits will also include analytical methods to measure the extent of tactic acid production, specifically lactic acid in order to determine functional aspects of the lactic acid producing bacteria. More typically, the kit also contains reagents for measuring acidity and capacity to produce lactic acid as well as the detection of the microorganisms responsible for the lactic acid production. The kit may contain reagents and equipment to measure pH of digesta or fascal material and fermentation tubes for measuring the potential lactic acid production with added carbohydrate. Both pH and lactic acid are typically detected using colour or other visual changes, spectrophotometric methods or through instruments such as pH metes.

More typically, the diagnostic kit may also contain antibodies capable of detecting microorganisms selected from the group consisting of: *Clostridium*-like species, *Prevaotella*-like species, *Bacteroides*-like species, *Enterococcus*-like species, *Selenomonas* species, non-dextran slime producing *Streptococcus* species and non-slime producing lactic acid bacterial isolates.

Even more typically, the diagnostic kit may also contain antibodies capable of detecting miroorganisms selected from the group consisting of: *Streptococcus equinus*, *Clostridium*-like *vitulinus*, *Selenomonas ruminantium*, *Prevotella*-like species, *Bacteroides*-like species, *Enterococcus*-like species, *Streptococcus bovis* SbR1 and non-slime producing lactic acid bacterial isolates LAB02, LAB06 and LAB08. Even more typically, the microorganism is selected from the group consisting of: *Streptococcus bovis* (SbR1), *Streptococcus equinus* (SER1); *Streptococcus equinus* (SER2); *Selenomonas ruminantium* (SRR1); *Selenomonas ruminantium* (SRR3); *Clostridium*-like *vitulinus* (LVR3); *Clostridium*-like *vitulinus* (LVR4), *Prevotella*-like isolates LAB01 and LAB03, *Bacteroides*-like isolates LAB07, *Enterococcus*-like isolate LAB05, *Streptococcus bovis* SbR1, non-dextran slime producing *Streptococcus* isolate LAB04 and non-slime producing lactic acid bacterial isolates LAB02, LAB06 and LAB08.

Yet still more typically, the microorganism(s) are selected from the group consisting of: *Streptococcus bovis* (SbR1) (NM99/04455), *Streptococcus equinus* (SER1) (NM99/04456); *Streptococcus equinus* (SER2) (NM99/04457); *Selenomonas ruminantium* (SRR1) (NM99/04458); *Selenomonas ruminantium* (SRR3) (NM99/04460); *Clostridium*-like *vitulinus* (LVR3) (NM99/04461); *Clostridium*-like *vitulinus* (LVR4) (NM99/04462); *Prevotella*-like LAB01 (NM00/12630) and LAB03 (NM00/12632), *Bacteroides*-like isolate LAB07 (NM00/12636); *Enterococcus*-like isolate LAB05 (NM00/12634), *Streptococcus bovis* (SbR1), non-dextran slime producing *Streptococcus* isolate LAB04 (NM00/12633) and non-slime producing lactic acid bacterial isolates LAB02 (NM00/12631), LAB06 (NM00/12635) and LAB08 (NM00/12637), together with *Streptococcus bovis* (strain Sb-5) deposited with the Australian Government Analytical Laboratories (AGAL) on 8 Mar. 1994, and given accession number N94/8255.

Typically, the kit may comprise the following containers:
(a) a first container containing at least the antibody (or fragment thereof) in accordance with the sixteenth embodiment of the invention, and;
(b) a second container containing a conjugate comprising a binding partner of the antibody (or fragment thereof), together with a detectable label.

More typically, the first container containing at least the antibody (or fragment thereof) in accordance with the sixteenth embodiment of the invention, may further comprise antibodies selected from the group consisting of: antibodies capable of detecting at least one lactic acid producing strain selected from *Streptococcus bovis* or lactobilli and antibodies capable of detecting *Streptococcus bovis* (strain Sb-5) deposited with the Australian Government Analytical Laboratories (AGAL) on 8 Mar. 1994, and given accession number N94/8255.

More typically, the kit may further comprise one or more other containers, containing other components, such as wash reagents, and other reagents capable of detecting the presence or bound antibodies. Even more typically, the detection reagents may include: labelled (secondary) antibodies, or whether the antibody (or fragment thereof) in accordance with the sixteenth embodiment of the invention is itself labelled, the compartment may comprise antibody binding reagents capable of reacting with the labelled antibody (or fragments thereof) of the present invention.

According to a nineteenth embodiment of the invention, there is provided a method for screening for the presence of microorganism having a role in acidosis in a vertebrate, said method comprising:

containing a sample from the gut of a vertebrate with the antibody (or fragment thereof) in accordance with the sixteenth embodiment of the invention; and (b) detecting the presence of the antibody (or fragment thereof) bound to microorganisms having a role in acidosis.

Typically, the antibody used in the method in accordance with the nineteenth embodiment of the invention corresponds to an antibody mix, comprising antibody or fragment thereof in accordance with the sixteenth embodiment of the invention, together with an antibody(s) selected from the group consisting of: antibodies capable of detecting at least one lactic acid producing strain selected from *Streptococcus bovis* or lactobacilli and antibodies capable of detecting *Streptococcus bovis* (strain Sb-5) deposited with the Australian Government Analytical Laboratories (AGAL) on 8 Mar. 1994, and given accession number N94/8255.

According to a twentieth embodiment of the invention, there is provided a method for screening for the presence of microorganisms having a role in acidosis in a vertebrate, said method comprising contacting a nucleic acid sample from a microorganism with a nucleic acid probe, wherein the microorganism is selected from the group consisting of: *Clostridium*-like species, *Prevotella*-like species, *Bacteroides*-like species, *Enterococcus*-like species, *Selenomonas* species, non-dextran slime producing *Streptococcus* species and non-slime producing lactic acid bacterial isolates, isolated from the gut of a vertebrate, and (b) detecting hybridisation between the nucleic acid sample and the polynucleotide sequence.

Typically, the microorganism is selected from the group consisting of: microorganisms selected from the group consisting of: *Streptococcus equinus*, *Clostridium*-like *vitulinus*, *Selenomonas ruminantium*, *Prevotella*-like species, *Bacteroides*-like species, *Enterococcus*-like species, *Streptococcus bovis* SbR1 and non-slime producing lactic acid bacterial isolates LAB02, LAB06 and LAB08. Even more typically, the microorganism is selected from the group consisting of: *Streptococcus bovis* (SbR1), *Streptococcus equinus* (SER1); *Streptococcus equinus* (SER2); *Selenomonas ruminantium* (SRR1); *Selenomonas ruminantium* (SRR3); *Clostridium*-like *vitulinus* (LVR3); *Clostridium*-like *vitulinus* (LVR4); *Prevotella*-like isolates LAB01 and LAB03, *Bacteroides*-like isolates LAB07, *Enterococcus*-like isolate LAB05, *Streptococcus bovis* SbR1, non-dextran slime producing *Streptococcus* isolate LAB04 and non-slime producing lactic acid bacterial isolates LAB02, LAB06 and LAB08.

Yet still more typically, the microorganism(s) is selected form the group consisting of: *Streptococcus bovis* (SbR1) (NM99/04455), *Streptococcus equinus* (SER1) (NM99/04456); *Streptococcus equinus* (SER2) (NM99/04457); *Selenomonas ruminantium* (SRR1) (NM99/04458); *Selenomonas ruminantium* (SRR3) (NM99/04460); *Clostridium*-like *vitulinus* (LVR3) (NM99/04461); *Clostridium*-like *vitulinus* (LVR4) (NM99/04462), *Prevotella*-like isolates LAB01 (NM00/12630) and LAB03 (NM00/12632), *Bacteroides*-like isolate LAB07 (NM00/12636), *Enterococcus*-like isolate LAB05 (NM00/12634), *Streptococcus bovis* (SbR1), non-dextran slime producing *Streptococcus* isolate LAB04 (NM00/12 631), LAB06 (NM00/12635) and LAB08 (NM00/12637).

Typically, hybridisation as compared to non-hybridisation is indicative of the presence of microorganisms having a role in acidosis.

Typically, the nucleic acid probe corresponds to a portion of the polynucleotide sequence in accordance with the twelfth or thirteenth embodiments of the invention which is capable of selectively hybridising to nucleic acid from a sample of gut microorganisms as defined in the first embodiment of the invention. More typically, the nucleic acid probe corresponds to a probe mix, comprising a portion of the polynucleotide sequence in accordance with the twelfth or thirteenth embodiments of the invention which is capable of selectively hybridising to nucleic acid from a sample, together with an isolated nucleic acid molecule comprising a polynucleotide sequence capable of selectively hybridising to the nucleic acid (or portion thereof) of at least one lactic acid producing strain selected from *Streptococcus bovis* or lactobacilli, or a polynucleotide sequence capable of selectively hybridising to the nucleic acid (or portion thereof) of the microorganism strain *Streptococcus bovis* (strain Sb-5) deposited with the Australian Government Analytical Laboratories (AGAL) on 8 Mar. 1994, and given accession number N94/8255.

Typically, hybridisation may occur and be detected through techniques that are routine and standard amongst those skilled in the art, and include southern and northern hybridisation, polymerase chain reaction (PCR) and ligase chain reaction (LCR) amplification.

Various low or high stringency hybridisation levels may be used, depending on the specificity and selectivity desired.

Typically, the microorganisms detected in accordance with the nineteenth or twentieth embodiment of the invention may also include lactic acid producing strain selected from *Streptococcus bovis* or lactobacilli. More typically, the microorganisms detected in accordance with the nineteenth or twentieth embodiment of the invention nay include *Streptococcus bovis* (strain Sb-5) deposited with the Australian Government Analytical Laboratories (AGAL) on 8 Mar. 1994, and given accession number N94/8255.

According to a twenty-five embodiment of the invention, there is provided a method for screening for potential therapeutic agents for the treatment of lactic acidosis in a vertebrate, said method comprising (a) contacting the potential therapeutic agent with a microorganism selected from the group consisting of: *Clostridium*-like species, *Prevotella*-like species, *Bacteroides*-like species, *Enterococcus*-like species, *Selenomonas* species, non-dextran slime producing *Streptococcus* species and non-slime producing lactic acid bacterial isolates, and (b) detecting an effect of the potential therapeutic agent on said microorganism.

Typically, the microorganism is selected from the group consisting of: microorganism selected from the group consisting of: *Streptococcus equinus, Clostridium*-like *vitulinus, Selenomonas ruminantium, Prevotella*-like species, *Bacteroides*-like species, *Enterococcus*-like species, *Streptococcus bovis* SbR1 and non-slime producing lactic acid bacterial isolates LAB02, LAB06 and LAB08. Even more typically, the microorganism is selected from the group consisting of: *Streptococcus bovis* (SbR1), *Streptococcus equinus* (SER1); *Streptococcus equinus* (SER2); *Selenomonas ruminantium* (SRR1); *Selenomonas ruminantium* (SSR3); *Clostridium*-like *vitulinus* (LVR3); *Clostridium*-like *vitulinus* (LVR4), *Prevotella*-like isolates LAB01 and LAB03, *Bacteroides*-like isolates LAB07, *Enterococcus*-like isolate LAB05, *Streptococcus bovis* SbR1, non-dextran slime producing *Streptococcus* isolate LAB04 and non-slime producing lactic acid bacterial isolates LAB02, LAB06 and LAB08.

Yet still more typically, the microorganism(s) is selected from the group consisting of: *Streptococcus bovis* (SbR1) (NM99/04455), *Streptococcus equinus* (SER1) (NM99/04456); *Streptococcus equinus* (SER2) (NM99/04457); *Selenomonas ruminantium* (SRR1), (NM99/04458); *Selenomonas ruminantium* (SRR3) (NM99/04460); *Clostridium*-like *vitulinus* (LVR3) (NM99/04461); *Clostridium*-like *vitulinus* (LVR4) (NM99/04462), *Prevotella*-like isolates LAB01 (NM00/12630) and LAB03 (NM00/12632), *Bacteroides*-like isolate LAB07 (NM00/12636), *Enterococcus*-like isolate LAB05 (NM00/12634), *Streptococcus bovis* (SbR1), non-dextran slime producing *Streptococcus* isolates LAB04 (NM00/12633) and non-slime producing lactic acid bacterial isolates LAB02 (NM00/12631), LAB06 (NM00/12635) and LAB08 (NM00/12637).

Typically, the screening method determines whether the potential therapeutic agent has a role in a lactic acid production pathway in at least one of the microorganisms of the invention. For example, the screening method in accordance with the twenty-first embodiment of the invention may identify a therapeutic agent which affects a critical step in the lactic acid biosynthetic pathway, such as blocking the conversion of pyruvate to lactate by inactivating the enzyme dehydrogenase, or blocking the conversion of malate to lactate by inactivating malo-lactic enzyme.

According to a twenty-second embodiment of the invention, there is provided an isolated culture of at least one microorganism selected from the group consisting of: *Streptococcus bovis* (SbR1) (NM99/04455); *Streptococcus equinus* (SER1) (NM99/04456); *Streptococcus equinus* (SER2) (NM99/04457); *Selenomonas ruminantium* (SRR1) (NM99/04458); *Selenomonas ruminantium* (SRR3) (NM99/04460); *Clostridium*-like *vitulinus* (LVR3) (NM99/04461); *Clostridium*-like *vitulinus* (LVR4) (NM99/04462); *Prevotella*-like isolates LAB01 (NM00/12630) and LAB03 (NM00/12632); *Bacteroides*-like isolate LAB07 (NM0-/12636); *Enterococcus*-like isolates LAB05 (NM00/12634), *Streptococcus bovis* (SbR1); non-dextran slime acid bacterial isolates LAB02 (NM00/12631), LAB06 (NM00/12635) and LAB08 (NM00/123637).

The term "antibody" means an immunoglobulin molecule able to bind to a specific epitope on an antigen. Antibodies can be comprised of a polyclonal mixture, or may be monoclonal in nature. Further, antibodies can be entire immunoglobulins derived from natural sources, or from recombinant sources. The antibodies of the present invention may exist in a variety of forms, including for example as a whole antibody, or as an antibody fragment, or other immunologically active fragment thereof, such as complementarity determining regions. Similarly, the antibody may exist as an antibody fragment having functional antigen-binding domains, that is, heavy and light chain variable domains. Also, the antibody fragment may exist in a form selected from the group consisting of: Fv, $F_{ab}$, $F(ab)_2$, scFv (single chain Fv), dAb (single domain antibody), bi-specific antibodies, diabodies and triabodies.

The term "isolated" means that the material in question has been removed from its host and associated impurities reduced or eliminated. Essentially, it means an object species is the predominant species present (ie., on a molar basis it is more abundant than any other individual species in the composition), and preferably a substantially purified fraction is a composition wherein the object species comprises at least about 30 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species.

As used herein the term "polypeptide" means a polymer made up of amino acids linked together by peptide bonds.

In the context of this specification, the term "comprising" means "including principally, but not necessarily solely". Further, variations of the word "comprising", such as "comprise" and "comprises" have correspondingly varied meanings.

BEST MODE OF PERFORMING THE INVENTION

Figure 1:
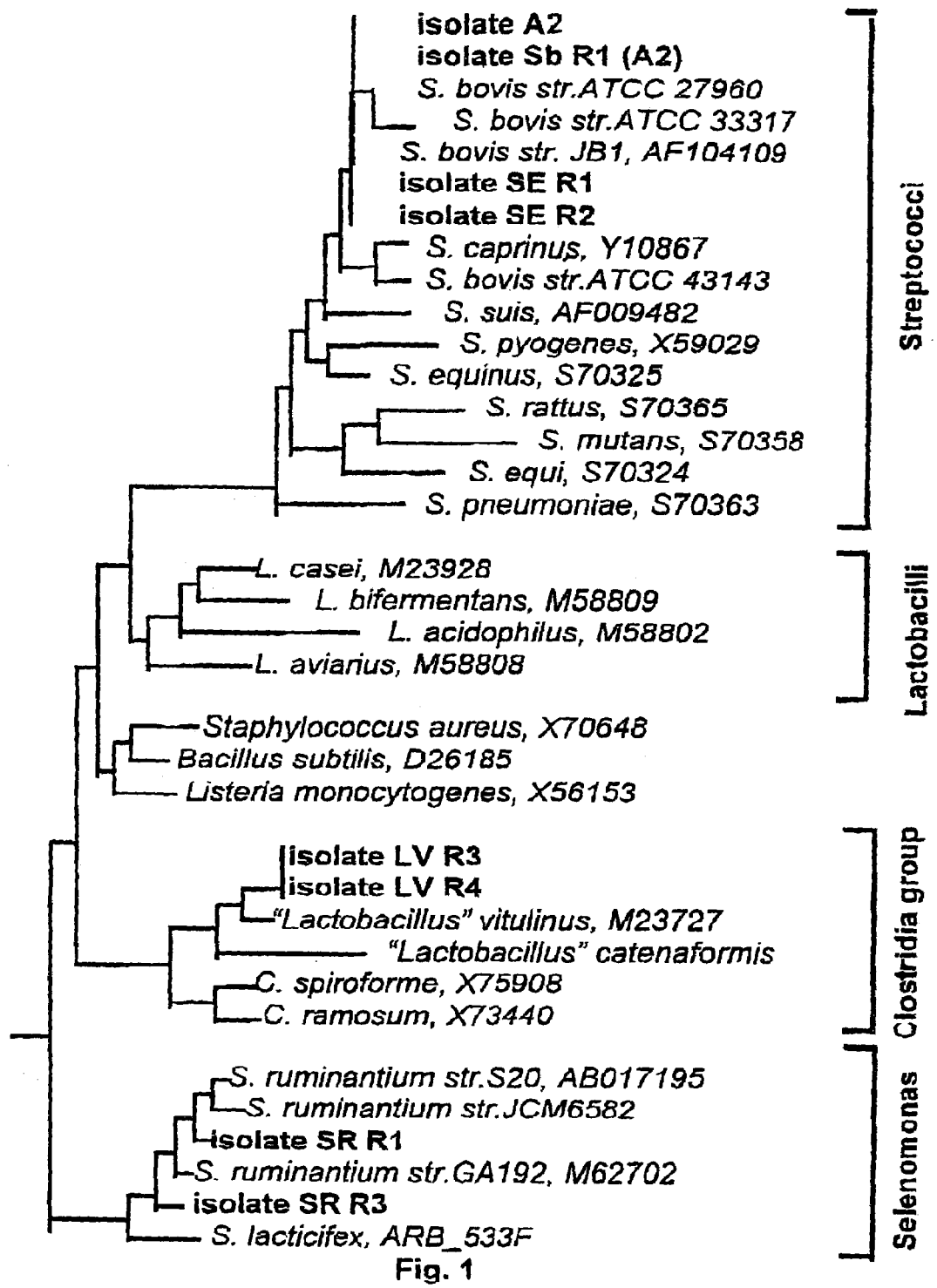
FIG. 1 describes a phylogenetic tree illustrating the phylogenetic relationship of the bacterial species and strains of the present invention.

1. Isolation of Microorganisms involved in acidosis

The following method provides a means of isolating microorganisms involved in acidosis. Fluid samples are taken from caecal, colonic, rectal or faecal material from animals or humans consuming a diet containing more than half of the dry matter as sugars, oligosaccharides or starch. This material (one part) may then be mixed well with distilled water (9 parts), prior to straining through 4 layers of cheese cloth and serially diluting in ten-fold steps using anaerobic dilution solution (ADS) (Caldwell and Bryant, 1966) to a final dilution of $10^{-8}$.

The material so diluted ($10^{-6}$, $10^{-7}$ and $10^{-8}$) is then used to inoculate media roll tubes prepared with modified semi-selective MRS-Agar medium, Oxoid, England, (de Man et al., 1960), together with adjustment of the pH of the medium to 5.5 Three replicate tubes are used for each dilution and they are incubated at 39° C. for three days.

The colonies so prepared are then carefully studied under a low power (×4) microscope to identify the most common colonies based on physical appearance and growth characteristics. These colonies are then enumerated at the three dilutions ($10^{-6}$, $10^{-7}$ and $10^{-8}$) to confirm a consistent representation. At this stage, samples are taken of at least five colonies that have been counted as being of the same most common characteristics to confirm similarity, and are examined under high power magnification (>40×) using gram straining to determine that the cells are similar.

Once this is done, viable colonies representing the dominant copy type are picked and used to inoculate a broth of basal medium 10 containing glucose (0.5%). This process of inoculation is repeated into MRS roll tubes and again examined for uniformity among colonies. At this stage, at least three examples of the most common colonies are examined and if these appear identical, representative colonies are picked and used to inoculate a broth of BM10. The process of roll tube and broth cultures is repeated until it is clear that a purified isolate has been obtained. In some cases, it is possible that two or more bacteria are very closely associated and in this case a crude isolate is maintained as the antigenic unit.

In the case of *Streptococcus* isolates, dextran (slime) characteristics are examined by centrifugation at 17,000 g for15 minutes. The absence of a bacterial "pellet" following centrifugation indicates a dextran type slime. One of the aims of the present invention was the selection for *S. bovis* bacterial that did not produce dextran slime.

Finally, characteristics of the isolate can then be determined by measuring the range of substrate utilisation and rate of lactic acid production.

2. Vaccine/Pharmaceutical Composition and Methods for Control of Acidosis

In a process of preparing a vertebrate vaccine of the invention, a typical protocol includes: washing the microbial growth free of nutrient medium, killing, harvesting and suspension of the dead cells of the microorganisms in a pharmaceutically/veterinarily acceptable carrier, diluent, excipient and/or adjuvant.

An alternative typical protocol includes: washing the microbial growth free of nutrient medium, rupturing to form outer membrane and associated proteins, separating whole cells from outer membranes and associated proteins, suspension of the outer membrane and associated proteins in a pharmaceutically/vertinarily acceptable carrier, diluent, excipient and/or adjuvant.

In delivery systems utilising the parenteral route it is preferred that dead cells of the microorganisms and/or outer membrane and associated proteins, are suitably washed, harvested and resuspended in a pharmaceutically/veterinarily acceptable carrier, diluent and/or adjuvant suitable for injection, utilising methods of administration as are well known in the art.

In the administration of therapeutic formulations in accordance with the present invention and herein disclosed, there are preferred non-toxic pharmaceutical carriers, diluents, excipients and/or adjuvants. For administration of the above formulations the microorganism or fragment or fragments thereof of the present invention are admixed with these non-toxic carriers, diluents, excipients and/or adjuvants and may be in the form of capsules, aqueous or oily suspensions, emulsions, micelles or injectable solutions.

Examples of pharmaceutically and veterinarily acceptable carriers or diluents are demineralised or distilled water; saline solution; vegetable based oils such as peanut oil, safflower oil, olive oil, cottonseed oil, maize oil, sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; crrageenan; gum tragcanth or gum acacia, and petroleum jelly. Typically, the carrier or carriers will form from 10% to 99.9% by weight of the compositions.

Adjuvants typically include emollients, emulsifiers, thickening agents, preservatives, bactericides, cytokines and buffering agents.

In general to induce the production of antibodies to the vaccines of the invention, they can be oleogenous or aqueous suspensions formulated in accordance with known methods in the art using suitable dispersing, suspension and/or wetting agents. Examples of suitable dispersing, suspension and wetting agents include Freund's complete/incomplete adjuvant. Montenide Marcol adjuvant and phosphate buffered saline, and mannan.

it will be appreciated that the examples referred to above are illustrative only and other suitable carriers, diluents, excipients and adjuvants known in the art may be employed without departing from the spirit of the invention.

For administration as an injectable solution or suspension, non-toxic parenterally acceptable diluents or carriers can include. Ringer's solution, isotonic saline, phosphate buffered saline, ethanol and 1,2 propylene glycol.

Further, a vaccine composition containing a recombinant polypeptide as encoded by at least one of the nucleic acid molecules in accordance with the twelfth or thirteenth embodiment of the invention, may be prepared for use by standard methods, well known to those of ordinary skill in the art.

In one embodiment, the immunogenic polypeptide, glycopeptide or the like, may be produced in a recombinant system by expression of the polynucleotide sequence (or a fragment thereof) in accordance with the twelfth or thirteenth embodiments of the invention, and subsequently isolated. For example, microbial cells containing the nucleic acid molecule of interest may be cultured in large volume bioreactors, then collected by centrifugation and subsequently ruptured, for instance by high-pressure homogenisation. The resulting cell lysate may be resuspended in appropriate diluent such as those described herein, and filtered to obtain an aqueous suspension of the immunogen. The recombinant protein can be administered in crude form, for example, by diluting in a 0.1M phosphate buffer (pH 7.4) to 50–500 $\mu$g/ml concentration, and then passing through a sterile 0.22 micron filter.

Alternatively, a vaccine composition containing the recombinant immunogenic polypeptide, glycopeptide or the like, may be prepared in a mammalian expression system, utilising host cells such as Chinese Hamster Ovary (CHO) cells. The recombinant polypeptide, glycopeptide or the like, (or fragment thereof) may be manufactured using batch fermentation with serum free medium. After fermentation the recombinant polypeptide, glycopeptide or the like, (or fragment thereof) may be purified via a multistep procedure incorporating chromatography and viral inactivation/removal steps. For instance, the recombinant polypeptide, glycopeptide or the like, (or fragment thereof) may be first separated by Protein A affinity chromatography and then treated with solvent/detergent to inactivate any lipid enveloped viruses. Further purification, typically by anion and cation exchange chromatography may be used to remove residual proteins, solvents/detergents and nucleic acids. The purified recombinant polypeptide glycopeptide or the like, (or fragment thereof) may be further purified and formulated into 0.9% saline using gel filtration columns. The formulated bulk preparation may then be sterilised and viral filtered and dispensed.

Alternatively, a vaccine composition containing an immunogenic polypeptide, glycopeptide or the like, of the microorganism of the present invention may be prepared by synthesis of a peptide, using standard methods known to those in the art, such as by automated synthesis on, for instance, an Applied Biosystems model 430A. For example, the peptide may comprise selected amino acid regions of the CDR and/or FR of the polypeptide of the invention. The synthetic peptide can be administered, for example, after diluting in a 0.1M phosphate buffer (pH 7.4) to 50–500 $\mu$g/ml concentration, and passing through a sterile 0.22 micron filter.

Alternatively, the vaccine may be a DNA based vaccine. In one aspect, the DNA based vaccine may comprise naked DNA comprising a nucleic acid encoding an immunogenic polypeptide of the microorganism of the present invention, or a fragment thereof.

In another aspect, the DNA based vaccine may comprise a nucleic acid molecule encoding an immunogenic polypeptide of the microorganism of the present invention, or a fragment thereof, cloned into an expression vector. Typically, the expression vector is a eucaryotic expression vector and may include expression control sequences, such as an origin of replication, a promoter, an enhancer, and necessary processing information sites, such as ribosome binding sites, RNA splice sites, polyadenylation sites, and transcriptional terminator sequences.

A typical vaccination regime is to deliver the vaccine in multiple doses generally one, two or three equal doses.

The vaccines of the invention are typically formulated for administration by parenteral route, by inhalation or topically, The term parenteral as used herein includes intravenous, intradermal, intramuscular, subcutaneous, rectal, vaginal or intraperitoneal administration. The subcutaneous and intramuscular forms of parenteral administration are generally preferred.

A vaccine or pharmaceutical composition of the invention may also be administered topically, such as externally to the epidermis, to the buccal cavity and instillation of such an antibody into the ear, eye and nose.

The amount of the vaccine or pharmaceutical composition of the invention required for therapeutic or prophylactic effect will, of course, vary with the vaccine or pharmaceutical composition chosen, the nature and severity of the condition being treated and the animal undergoing treatment, and is ultimately at the direction of the physician or veterinarian. A suitable topical dose of a vaccine or pharmaceutical composition of the invention will generally be within the range of about 1 to about 100 milligrams per kilogram body weight daily; preferably about 0.05 to about 50, more preferably about 0.5 to about 25, even more preferably about 0.5 to about 10 milligrams per kilogram body weight per day.

The parenteral dosage regimens for employing compounds of the invention to prophylactically or therapeutically control lactic acidosis will generally be in the range of about 0.01 to about 100, preferably about 0.01 to about 50, more preferably about 0.05 to about 25, even more preferably about 0.1 to about 2 milligrams per kilogram body weight per day. Alternatively, dosage rates can be determined in relation to metabolic rate or surface area of the body.

A vaccine or pharmaceutical composition of the invention may also be administered by inhalation, that is, intranasal and/or inhalation administration. Appropriate dosage forms for such administration, such as an aerosol formulation or a metered dose inhaler, may be prepared by conventional techniques. The preferred dosage amount of a compound of the invention to be employed is generally within the range of about 0.05 to about 100, preferably about 0.05 to about 50, more preferably about 0.5 to about 25, even more preferably about 0.5 to about 10 milligrams per kilogram body weight per day.

Typically, the dosage rate for immunisation is between $1 \times 10^6$ and $1 \times 10^{11}$ bacterial cells per administration.

Typically, the dosage rates are approximately equivalent to between $1 \times 10^8$ to $1 \times 10^9$ bacterial cells per kg body weight. More typically, the dosage rates are approximately equivalent to between $1 \times 10^8$ and $5 \times 10^8$ bacterial cells per kg body weight. Even more typically, the dosage rates are approximately equivalent to $2.5 \times 10^8$ bacterial cells per kg body weight.

Typically, the dosage rate for immunisation of small animals, such as sheep, is between $1 \times 10^9$ and $5 \times 10^{10}$ bacterial cells per injection. More typically, the dosage rate for immunisation of small animals, such as sheep, is approximately $5 \times 10^9$ bacterial cells per administration.

Typically, the dosage rate for immunisation of large animals, such as cattle and horses, is between $1 \times 10^9$ and $1 \times 10^{12}$ bacterial cells per injection. More typically, the dosage rate for immunisation of large animals, such as cattle and horses, is approximately $1 \times 10^{10}$ bacterial cells per administration.

Typically, the injection volume for sheep is between 1 mL to 3 mL, and 2 to 7 mL for cattle and horses 3 to 5 mL. More typically, the injection volume for sheep is between 1 mL to 2 mL, and 1 to 5 mL for cattle and horses.

In accordance with any one of the third through eleventh embodiments of the invention, the administered dose of the antibiotic can vary and will depend on several factors, such as the condition, age and size of the human or animal patient, as well as the nature of the lactic acid producing bacteria.

Dosages will typically range from between any one of the following: 0.01 and 100 mg per kg of bodyweight; 0.01 and 75 mg per kg of bodyweight; 0.01 and 50 mg per kg of bodyweight; 0.01 and 25 mg kg of bodyweight; 0.01 and 15 mg per kg of bodyweight; 0.01 and 10 mg per kg of bodyweight; and 0.01 and 5 mg per kg of bodyweight. More typically dosages will range from between 0.2 and 2.0 mg per kg of bodyweight. More typically dosages will range from between 0.5 and 1.0 mg per kg of bodyweight. Even more typically dosages will range from between 0.1 and 0.5 mg per kg of bodyweight. Yet even more typically, the antibiotic is administered to the human or animal at a rate of 0.4 mg per kg of bodyweight.

Typically, the antibiotic is administered at a rate of between 1 and 100 mg per kg of dry weight of food. More typically, the antibiotic is administered at a rate of between 1 and 75 mg per kg of dry weight or food. Even more typically, the antibiotic is administered at a rate of between 1 and 50 mg per kg of dry weight of food. Yet even more typically, the antibiotic is administered at a rate of between 5 and 40 mg per kg of dry weight of food.

Typically, antibiotic preparations are selected and/or formulated for delivery to the hind gut and for little or no absorption from the digestive tract. Formulations include encapsulation and/or coating with materials resistant to acid and enzymatic digestion in the stomach and small intestine. Formulation can also include chemical treatment to reduce the solubility of the antibiotic.

As above, the administered dose of the enzyme preparation can vary and will depend on several factors, such as the condition, age and size of the human or animal patient, as well as the nature of the carbohydrate. Dosages will typically range from between 0.01 and 50 g/kg food dry matter. Typically, the enzyme is administered at a rate of between 0.1 and 3 g per kg of dry weight of food. More typically, the enzyme is administered at a rate of between 1 g per kg of dry weight of food.

Similarly, the administered dose of the clay preparation can vary and will depend on several factors, such as the condition, age and size of the human or animal patient, as well as the nature of the carbohydrate. Dosages will typically range from between 0.5 and 100 g/kg food dry matter. Typically, the clay is administered at a rate of between 1 and 50 g per kg of the dry weight of food. More typically, the clay is administered at a rate of between 10 and 20 g per kg of dry weight of food.

Typically, the administered dose of the probiotic preparation can vary between $10^4$ and $10^{12}$ bacteria per kg of body weight. More typically, dose of the probiotic preparation can vary between $10^4$ and $10^{10}$ per kg of body weight. Even more typically, dose of the probiotic preparation can vary between $10^4$ and $10^6$ per kg of body weight.

Typically, probiotics are formulated in such a way as to deliver viable bacteria and/or other microorganisms to gastrointestinal tracer including the hind gut. These formulation techniques include coatings and encapsulation using materials resistant to gastric and intestinal digestion.

According to another form of the invention, the active agents can be used together.

According to another aspect of the invention, the formulation of the active agent ensures that it is administered in a palatable form to the animal or human and in a form which retains activity and is properly mixed in the appropriate compartment(s) of the gastrointestinal tract.

Generally, the active agent is administered regularly throughout the period the animal or human is subjected to a high carbohydrate diet or to sugars or other fermentable compounds which are not efficiently absorbed prior to reaching the large intestine, colon and caecum.

More typically, the active agent is administered 1–3 times daily. Even more typically, the active agent is administered once daily or can be included in human food and animal feeds. They can be fed as powders or suspended in water, included in pellets as well as being fed in premixes.

More typically the active agent is mixed with the food, or is added to feeds which contain starch or sugars which may produce an acidic pattern of fermentation in the gastrointestinal tract. The active agent can also be added to water included in tablets and the like.

A suitable treatment may include the administration of a single dose or multiple doses. Usually, the treatment will consist of administering one dose daily of the active agent for a period sufficient to control the accumulation of acid by fermentation of the carbohydrate in the gastrointestinal tract. Dosing may continue while sources of carbohydrate known to cause problems of acidic fermentation in the gastrointestinal tract are included in the diet.

More typically the active agent may be administered in a single dose immediately before consuming meals containing sources of carbohydrate which are poorly digested and rapidly fermented.

More typically, the active agent is administered for only day prior to and daily during the consumption of excessive quantities of food stuffs containing readily fermentable carbohydrates.

Typically, the active agent is administered orally.

3. Antibiotics

Antibodies or immunoglobulins are typically composed of four covalently bound peptide chains. For example, an IgG antibody has two light chains and two heavy chains. Each light chain is covalently bound to a heavy chain. In turn each heavy chain is covalently linked to the other to form a "Y" configuration, also known as an immunoglobulin conformation. Fragments of these molecules, or even heavy or light chains alone, may bind antigen.

A normal antibody heavy or light chain has an N-terminal ($NH_2$) variable (V) region, and a C-terminal (COOH) constant (C) region. The heavy chain variable region is referred to as $V_H$ (including, for example, $V_\gamma$), and the light chain variable region is referred to as $V_L$ (including $V_\kappa$ or $V_\lambda$). The variable region is the part of the molecule that binds to the antibody's cognate antigen, while the Fc region (the second and third domains of the C region) on the heavy chain determines the antibody's effector function (eg. complement fixation, opsonization). Full-length immunoglobulin or antibody "light chains" are encoded by a variable region gene at the N-terminus and a κ (kappa) or λ (lambda) constant region gene at the COOH-terminus. Full-length immunoglobulin or antibody "heavy chains", are similarly encoded by a variable region gene and one of the constant region genes, e.g., gamma. Typically, the "$V_L$" will include the portion of the light chain encoded by the $V_L$ and $J_L$ (J or joining region) gene segments and the "$V_H$" will include the portion of the heavy chain encoded by the $V_H$, and $D_H$ (D or diversity region) and $J_H$ gene segments.

An immunoglobulin, light or heavy chain variable region consists of a "framework" region interrupted by three hypervariable regions, also called complementarity-determining regions or CDRs. The sequences of the framework regions of different light or heavy chains are relatively conserved within a species. The framework region of an antibody, that is the combined framework regions of the constituent light and heavy chains, serves to position and align the CDRs in three dimensional space. The CDRs are primarily referred to as CDR1, CDR2, and CDR3, numbered sequentially starting from the N-terminus.

The two types of light chains, κ (kappa) and λ (lambda), are referred to as isotopes. Isotypic determinants typically reside in the constant region of the light chain, also referred to as the $C_L$ in general, and $C_\kappa$ or $C_\lambda$ in particular. Likewise, the constant region of the heavy chain molecule, also known as $C_H$, determines the isotype of the antibody. Antibodies are referred to as IgM, IgD, IgG, IgA, and IgE depending on the heavy chain isotype. The isotopes are encoded in the λ (mu), δ (delta), γ (gamma), α (alpha), and ε (epsilon) segments of the heavy chain constant region, respectively.

The heavy chain isotopes determine different effector functions of the antibody, such as opsonisation or complement fixation. In addition, the heavy chain isotype determines the secreted form of the antibody. Secreted IgG, IgD, and IgE isotypes are typically found in single unit or monomeric form. Secreted IgM isotype is found in pentameric form; secreted IgA can be found in both monomeric and dimeric form.

In a related aspect, the invention features a monoclonal antibody, or an Fab, $(Fab)_2$, scFv (single chain Fv), dAb (single domain antibody), bi-specific antibodies, diabodies and triabodies, or other immunologically active fragment thereof (eg., a CDR-region). Such fragments are useful as immunosuppressive agents. Alternatively, the antibodies of the invention may have attached to it an effector or reporter molecule. For instance, an antibody or fragment thereof of the invention may have a macrocycle, for chelating a heavy metal atom, or a toxin, such as ricin, attached to it by a covalent bridging structure. In addition, the Fc fragment or $CH_3$ domain of a complete antibody molecule may be replaced or conjugated by an enzyme or toxin molecule, such as chelates, toxins, drugs or prodrugs, and a part of the immunoglobulin chain may be bonded with a polypeptide effector or reporter molecule, such as biotin, fluorochromes, phosphatases and peroxidases. Bispecific antibodies may also be produced in accordance with standard procedures well known to those skilled in the art.

The present invention further contemplates genetically modifying the antibody variable and/or constant regions to include effectively homologous variable and constant region amino acid sequences. Generally, changes in the variable region will be made to improve or otherwise modify antigen binding properties of the antibody or fragment thereof. Changes in the constant region will, in general, be made in order to improve or otherwise modify biological properties, such as complement fixation, interaction with membranes, and other effector functions.

Typically, the antibodies in accordance with the sixteenth embodiment of the invention can be comprised of a polyclonal mixture, or may be monoclonal in nature. Further, antibodies can be entire immunoglobulins derived from natural sources, or from recombinant sources. The antibodies of the present invention may exist in a variety of forms, including for example as a whole antibody, or as an antibody fragment, or other immunologically active fragment thereof, such as complementarity determining regions.

Monoclonal antibodies can be obtained by various techniques familiar to those skilled in the art. For example, spleen cells from an animal immunised with a desired antigen are immortalised, commonly by fusion with a myeloma cell, in a manner as described for example, in Kohler and Milstein, Eur. J. Immunol., 6:511–519 (1976), the disclosure of which is incorporated herein by reference.

Alternative methods of immortalisation include transformation with Epstein Barr Virus, oncogenes, or retroviruses, or other methods well known in the art. Colonies arising from single immortalised cells are screened for production of antibodies of the desired specificity and affinity for the antigen, and yield of the monoclonal antibodies produced by such cells may be enhanced by various techniques, including injection into the peritoneal cavity of a vertebrate host. Various techniques useful in these arts are discussed, for example, in Harlow and Lane, Antibodies: A Laboratory Manual, Cold Spring Harbor, New York, (1988), the disclosure of which is incorporated herein by reference, including: immunisation of animals to produce immunoglobulins; production of monoclonal antibodies; labelling immunoglobulins for use as probes; immunoaffinity purification; and immunoassays.

4. An antibody/nucleic acid based method and kit for detecting acidosis activity The present invention also encompasses a method of detecting in a sample the presence of microorganisms involved in lactic acidosis and/or the potential acid producing characteristics of the microorganisms, wherein the method comprises:

(a) contacting a sample with the antibody (or fragment thereof) as defined in accordance with the sixteenth embodiment of the invention, and (b) detecting the presence of the antibody (or fragment thereof) bound to a microorganism or (fragment thereof) involved in lactic acidosis.

Typically, the method of detecting in a sample the presence of microorganisms involved in lactic acidosis, or potential lactic acid producing microorganisms may also comprise:

(c) measuring lactic acid present in the digesta or faecal sample or measuring pH of said sample; or (d) measuring amount of lactic acid produced when microorganisms ferment carbohydrate.

Conditions for incubating an antibody (or fragment thereof) with a test sample vary widely, depending on the format of detection used in the assay, the detection method, and the type and nature of the antibody used. A person of ordinary skill in the art would readily appreciate that any one of the commonly available immunological assays could be used in performing the method of detection. For example, these assays include: radio immunoassays, enzyme-linked immunosorbent assays, and/or immunoflourescent assays.

A kit for performing the above method of the invention contains all the necessary reagents to carry out the above methods of detection. For example, the kit may comprise the following containers:

(a) a first container containing the antibody (or fragment thereof) in accordance with the sixteenth embodiment of the present invention;

(b) a second container containing a conjugate comprising a binding partner of the antibody (or fragment thereof), together with a detectable label.

Typically, the kit may further comprise one or more other containers, containing other components, such as wash reagents, and other reagents capable of detecting the presence of bound antibodies. More typically, the detection reagents may include: labelled (secondary) antibodies, or where the antibody (or fragment thereof) of the present invention is itself labelled, the components may comprise antibody binding reagents capable of reacting with the labelled antibody (or fragment thereof) of the present invention.

Further, the kit of the present invention, as described above in relation to antibodies, can be readily incorporated, without the expenditure of inventive ingenuity, into a kit for nucleic acid probes. One skilled in the art would select the nucleic acid probe from the polynucleotides of the present invention, according to techniques known in the art as described above. Samples to be tested include but should not be limited to RNA samples of vertebrate tissue.

Such a kit comprises at least one container means having disposed therein the above-described nucleic acid probe. The kit may further comprise other containers comprising one or more of the following: wash reagents and reagents capable of detecting the presence of bound nucleic acid probe. Examples of detection reagents include, but are not limited to radiolabelled probes, enzymatic labelled probes (horseradish peroxidase, alkaline phosphatase), and affinity labelled probes (biotin, avidin, or steptavidin).

In detail, a compartmentalised kit includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the test sample, a container which contains the probe or primers used in the assay, containers which contain wash reagents (such as phosphate buffered saline, Tris-buffers, and like), and containers which contain the reagent detect the hybridised probe, bound antibody, amide product, or the like.

Furthermore, one skilled in the art would readily recognise that the nucleic acid probes of the present invention can readily be incorporated into one of the established kit formats, which are known in the art.

In terms of measuring lactic acid production, the pH of digesta or faecal material can be measured using colour sensitive reagents or a pH meter. Lactic acid can be detected using colorimetric techniques using enzymes, colour reagents and assays assessed with the naked eye or using spectrometric techniques. Further, identifying potential lactic acid producing bacteria involves incubation of the sample with carbohydrate followed by measurement of lactic acid, pH and lactic acid producing bacteria.

The invention will now be described in greater detail by reference to specific Examples, which should not be construed as in any way limiting on the scope thereof.

EXAMPLES

Example 1

Control of *S. ruminantium, Clostridium*-like *vitulinus, S. bovis* and *S. equinus*

Material and Methods

Isolation, Identification and characterisation of lactic acid producing bacteria The following method was used to isolate the most numerous and most prolific acid-producing bacteria in the gut contents of ruminant and non-ruminant animals. Rumen fluid samples were obtained via stomach tube from sheep and via rumen fistula from cattle 24 h after regular grain feeding. Faecal samples were obtained directly from the rectum of sheep and cattle and from the freshly voided faeces from horses. Samples were processed for the enumeration of lactic acid bacteria following the method of Yanke and Cheng (1998) involving one-hour exposure prior to incubation. A semi-selective MRS-agar medium, Oxoid, England (De Man et al. 1960) was modified by adding a freshly prepared reducing solution (1 ml containing 0.02 g Cysteine, HCl and 0.026 g of $Na_2S.9H_2S.9H_2O$ per 100 ml of media) after boiling then pre-reduced by bubbling with $CO_2$ on ice until cold. The pH of the medium was adjusted to 5.5 during preparation. Viable colonies from roll tubes were picked and incubated into a broth of a basal medium 10 (BM 10) as described by Caldwell and Bryant (1966) with glucose (0.5%) and then again cultured in roll tubes. The procedure of picking colonies and inoculating them into a broth medium followed by inoculating again into roll tubes was repeated twice. At 48 h of incubation a drop of the broth medium was examined under the microscope to check the purity of the culture. Morphology and Gram staining characteristics of the isolates were recorded. The ability of cultures to ferment various carbohydrates was evaluated using a broth of BM10 with each isolate included at 2 g/L. *S. bovis* was distinguished from *S. equinus* on the basis of their ability to ferment starch, insulin and lactose and their ability to survive heating to 60° C. for 30 minutes was also tested (Hardie 1986).

Fermentation products were measured after 24 h of anaerobic incubation of a broth consisting of BM 10 with glucose or starch (0.5%) at 39° C. At the end of the fermentation period, samples from the media were taken for measurements of pH, then acidified with sulphuric acid for further analysis of VFA and lactate. VFA concentrations were measured using a gas chromatographed (Packard Model 427, Packard Instrument Company, Inc., Illinois, USA), fitted with a Chromsorb 'W', acid washed and 60–80 mesh column coated with two liquid phases, a: o-phosphoric acid (1.5% w/w) and b: Polypropylene glycol sebacate (17.5% w/w). The temperature for the column, detector and the injector was 135, 180 and 210° C. respectively. L-lactate and D-lactate were analyzed by auto-analyzer (Cobas Mir Autoanalyzer, Roche Diagnostics Inc., French Forest, NSW) using an enzymatic procedure (Stat-Pack™ Rapid Lactate Test, Cat No. 1112 821, Behring Diagnostics Inc., Somerville, N.J.). The 16S rRNA complete gene sequencing and DNA hybridisation techniques (Lane, 1991) were used to identify the most prevalent strains of S. bovis, Clostridium-like vitulinus and S. ruminantium.

Virginiamycin sensitivity test

Two isolates of S. bovis from cattle and sheep (orange pigmented and white), five Clostridium-like vitulinus and three isolates of S. ruminantium were incubated in a branch of basal medium 10 with glucose (0.5%) and virginiamycin (VM) at a concentrations of 0, 2, 4, 6 and 8 $\mu$g/ml. The virginiamycin solution (100 $\mu$g VM/ml) was prepared using Eskalin Wettable Powder (WP), 400 g/kg VM (Pfizer Animal Health, NSW, Australia). The WP was dissolved in distilled water (previously boiled and bubbled with nitrogen until cooled) and filter-sterilised whilst being gassed with nitrogen. This solution was used immediately after preparation. The lowest concentration of VM that resulted in no measurable growth of the test bacteria was considered as the Minimum Inhibitory Concentration (MIC). The broth-media was inoculated by 0.2 ml of the different fresh viable cultures and 0.1–0.4 ml of VM solution was added to each tube to provide the required dose. A sensitivity test was also performed when VM was added 3 and 6 h after inoculation, using the same concentrations of VM. Tests for sensitivity to VM were conducted using 24 and 4 h h of anaerobic incubation at 39° C.

DNA extraction, PCR amplification and cloning

Freshly grown cultures were withdrawn from screw-cap Hungate tubes by first flaming the septum with ethanol. Sub-samples (0.6 ml) of liquid culture were taken with a 25G needle and placed in sterile 1.5-mL centrifuge tubes. Cells were harvested as a pellet following centrifugation at 13500 g for 2 min. The supernatant was poured off and the cells resuspended in approximately 30 $\mu$L of culture fluid remaining.

DNA was extracted form the concentrated cell suspension using a Fast DNA SPIN KIT (BIO 101, Inc, CA). Extracted DNA was visualized on a 1% TAE gel amended with 0.5 $\mu$l of 10 mg/kg ethidium bromide per 50 mL agarose. PCR was used to amplify 16S rDNAs in 100 $\mu$L reactions. Each reaction tube contained 200 ng of each primer, 10 $\mu$l of 10× buffer, 6 $\mu$L of MgCl$_2$, 1 U of Tth DNA polymerase (Biotech International, Perth, Australia), 10 $\mu$L of 4×0.5 mM dNTP's, and the remainder made up with sterile Milli-Q water and 2 $\mu$L concentrated cell suspension or DNA extract. Reactions were overlaid with sterile mineral oil and carried out in a thermocycler (Perkin-Elmer DNA Thermal Cycler 480). Thermocycling parameters employed after at 96° C., denaturation for 10 min were 28 cycles of 1 min at 94° C., 1 min at an annealing temperature, and 2 min at 72° C. A further extension step involving 1 min at 48° C. and 5 min at 72° C. was also employed. The primers used were 27f (5'-AGAGTTTGATCCTGGCTCAG-3') (SEQ ID No:8) and 1492r (5'-GGTTACCTTGTTACGACT-3') (SEQ ID No;9) (Lane 1991). In some cases GeneReleaser (Bioventures Inc., Tennessee, USA) was used according to the manufacturer's instructions in the reactions outlined above. PCR products were purified using a QIAquick PCR purification kit (QIAGEN, Victoria Australia) according to the manufacturer's instructions.

Sequencing of 16S rDNA

All 16S rDNA samples were initially partially sequenced using the universal 16S rRNA primer, 530f (5'-GTGC-CAGCMGCCGCCG-3') (SEQ ID No:10) and an ABI Big Dye Terminator Cycle Sequencing Ready Reaction Mix kit (Victoria, Australia). Selected 16S rDNA were subsequently fully sequenced on both strands using the following primers: 519r (5'-GWATTACCGCGGCKGCTG-3') (SEQ ID No:11), 27f, 907r (5'-CCGTCAATTCMTTTRAGTTT-3') (DEQ ID No:12), 926f (5'AAACTYAAAKGAATTGACGG-3') (SEQ ID No:13).

Approximately 100 ng of purified PCR product and 25 ng of primer were used in the sequencing reactions. Thermal cycling was carried out in an MJ Research PTC-100 thermocycler with an initial denaturation step of 96° C. for 2 min, following by 25 cycles of 50° C. for 15s, 60° C. for 4 min, and 96° C. for 30s. The resulting cycle sequencing products were purified using the ethanol plus sodium acetate method (ABI, Australia). Purified sequencing products were submitted to the Australian Genome Research Facility for analysis on an Applied Biosystems 377 automated sequencer.

Phylogenetic analysis

Phylogenetic analysis of 16S rDNA's was carried out according to Dojka et al. (1998). Briefly, sequences were aligned and compiled in SeqEd (Applied Biosystems Australia). Compiled sequences were compared with those on publicly available databases by use of the BLAST (Basic Alignment Search Tool) (Altschul et al. 1990) to determine approximate phylogenetic affiliations. Compiled sequences were then aligned using the ARB software package (Strunk et al. unpublished) and refined manually. Phylogenetic trees based on comparative analysis of the 16S rRNA genes were construction by performing evolution distance analyses on these alignments using the appropriate tool in the ARB database. The robustness of the tree topology was tested by performing bootstrapping (2000 replicates) in PAUP test version 4.0d65.

Results

All twenty streptococcal isolates (6 from sheep, 2 from cattle and 12 from horses) were 99% identical in sequence to each other and to S. bovis and S. equinus. These isolates therefore belong to the genus Streptococcus and are members of either S. bovis or S. equinus. Three of the 12 streptococcal isolates from horses were identified, as S. equinus as they did not ferment starch or insulin and only one of them fermented lactose.

Sb R1 was the dominant S. bovis strain across all three animal species (cattle, sheep and horse). It grows into bright orange-centered colonies on MRS agar roll tubes and produces an orange pigment in a broth of BM 10 with glucose or starch. The cells are 0.9–1.0 μm in diameter and often encapsulated, occurred mainly in pairs, short chains of 4–10 cells and singles. The doubling time for *S. bovis* was estimated to be 24 minutes. Three streptococcal isolates (SE R1, SE R2 & SE R3) from horses were identified as *S. equinus*. The cells occurred mainly in long chains.

Table 1 shows the fermentation end products of *S. bovis, S. equinus, Clostridium*-like *vitulinus* and *S. ruminantium* isolates. All of the *S. bovis* bacteria could ferment cellobiose, fructose, galactose, glucose, lactose, maltose, mannose, raffinose, starch and sucrose, but not arabinose, glycerol, mannitol, ribose, sorbitol or xylose and two of the white pigments isolates did not ferment insulin (Table 2). L-lactate was the main fermentation product of *S. bovis* and *S. equinus*.

The *Clostridium*-like *vitulinus*-like isolates have 100% sequence identity to each other, and 97% identity with *Clostridium*-like *vitulinus*. *Clostridium*-like *vitulinus* cells occurred in different shapes and sizes, mainly straight rods in singles, pairs and short chains and some cells have the tendency to branch. *Clostridium*-like *vitulinus* isolates could not ferment starch or xylose but grew on cellobiose, fructose, glucose, mannose, raffinose and sucrose (Table 2). Two *Clostridium*-like *vitulinus* isolates produced D-lactate and one produced L- and D-lactate at equal proportions.

*S. ruminantium* was isolated from the rumen of grass-adapted sheep that received a grain supplement with or without virginiamycin. The three *Selenomonas*-like isolates formed two distinct lines of descent: Type A (isolate SR R1); and Type B (isolate SR R2 and isolate SR R3). Type A has >97% identity to *S. ruminantium*. This indicates that all three isolates are members of the genus *Selenomonas* and Type A belongs to the species *S. ruminantium*. One isolate (SR R1) produced L-Lactate while the other two (SR R2 and SR R3) produced L- and D-lactate (Table 3). A difference between SR R2 and SR R3 was that SR R3 produced 42.5% more lactic acid from starch than SR R2. *S. ruminantium* grew on most carbohydrate sources (Table 2) but their growth was noticeably high on glucose and sucrose compared with other sources and only one isolate (SR R1) did not ferment starch. The cells are 0.5–0.7×1.5–3.0 μm, occurred mainly in single short crescent rods, with round ends and Gram-negative. Similar amounts of L-lactate were produced from glucose, starch or raftilose by the different *S. bovis* isolates (Table 4).

Incubation in vitro of *S. bovis, Clostridium*-like *vitulinus* and *S. ruminantium* isolates in a broth of Basal Medium 10 with glucose (0.5%) with different concentration of VM (0, 2, 4, 6 and 8 μg/ml) clearly demonstrated sensitivity of *S. bovis* to virginiamycin. *Clostridium*-like *Selenomonas* isolates (Table 5) showed varying levels of resistance to VM. LV R1 and LV R5 were very sensitivity to VM with a MIC level of 2 μg/ml. Isolates LV R2 and LV R3 resisted levels up to 4 μg/ml and LV R4 up to 6 μg/ml. *S. ruminantium* isolates were resistant to the highest VM levels (8 μg/ml). Sensitivity of *Clostridium*-like bacteria to VM was different when VM was added at 3 and 6 h after inoculation. All *Clostridium*-like cultures growing for 3 h before the addition of VM had higher MIC than when VM was added to immediately after inoculation. Sensitivity to VM was also lower when assessed using a 48 h incubation. All *Clostridium*-like isolates were resistant to the highest VM levels (8 μg/ml) when cultures were allowed to grow for 6 h before the addition of VM.

Discussion

The presence of *Clostridium*-like *vitulinus* and *S. ruminantium* in rumen fluid and the faeces of sheep fed diets with or without VM demonstrated the resistance of some *Clostridium*-like strains to viginiamycin (VM). This resistance of *Clostridium*-like and *Selenomonas* isolates has been confirmed by results from anaerobic in vitro incubation of in a broth of BM 10 with glucose (0.5%) with or without VM.

A sensitivity test showed that *S. bovis* strains are quite sensitive to VM and this reaction seems to be irreversible and fatal. On the other hand the reaction of *Clostridium*-like cells to VM with may be reversible one and the initial reaction results in only bacteriostasis rather than bactericidal effects.

The fact that the Gram-negative bacteria *S. ruminantium* i snot sensitive to VM suggests that there will be situations where are VM may not provide for protection against acidosis. Godfrey et al. (1995) and Nagaraja et al. (1995) reported that in grain-adapted sheep the inclusion of VM with grain did not prevent decreased ruminal pH and increased lactate. This may indicate that under conditions where *Clostridium*-like bacteria and *Selenomonas* are well established in the gut, the use of VM may not be as effective in controlling acidosis.

These results also indicate why vaccination against *S. bovis* alone is unlikely to effectively control lactic acid accumulation when animals consume high levels of readily fermentable carbohydrates. Under these are conditions *Selenomonas* and *Clostridium*-like will continue to produce lactic acid even if the activity of *S. bovis* is inhibited.

It is clear that any diagnosis, vaccine or other method to prevent or control fermentative acidosis should detect and or be active against at least *S. ruminantium, Clostridium*-like *vitulinus, S. bovis* and *S. equinus*.

Example 2

Samples of faeces were collected from 12 horses fed a mixture of chopped leucerne hay and different types of cereal grain (oats, barley, triticale and sorghum). The dominant lactic acid producing bacteria were isolated using the same method as described in Example 1. Two bacteria were isolated: *Streptococcus bovis* (SbR1) and *Streptococcus equinus* (SER1 and SER2). Based on these results it is important that any vaccine, diagnosis or other treatment to prevent or control acidosis should be effective against both *S. bovis* and *S. equinus*. Under some conditions it will also be necessary for these diagnostic tools and methods of treatment to be effective against *S. ruminantium, Clostridium*-like *vitulinus* as well as *S. bovis* and *S. equinus*.

In certain conditions it is likely that *Selenomonas ruminantium* and *Clostridium*-like *vitulinus* bacteria may be present and in this case animals should be vaccinated against both Gram-positive and Gram-negative lactic acid producing bacteria.

Example 3

Following calving, cows grazing lush green pasture are exposed to high levels of soluble carbohydrate in the form of fructans in grasses and sugars and starch in clovers. In addition to fermentable carbohydrates in the pasture, concentrate feed supplements, based on cereal grain, are fed twice daily during milking. The fructants in pastures and the starch in legumes and concentrate are rapidly fermented in either the rumen or the hind gut to form a range of volatile fatty acids and lactic acid. The accumulation of acids in the gut contribute to the metabolic acid load of the animal, can cause inflammation of the gut wall leading to stimulation of the immune system and can lead to increased pathogenicity in the populations of bacteria and parasites within the gut. The adverse effects of acid accumulation in the gut result in reduced productivity and an increased incidences of disease including lameness, respiratory conditions and mastitis.

Acid accumulation in the gut under this dietary regime can be satisfactorily reduced by controlling two of the principle acid producing bacteria *Selenomonas ruminantium* and *Streptococcus* spp. As one of these bacteria is Gram-negative and the other Gram-positive two approaches are used. A vaccine is used to control *Selenomonas ruminantium* and the feed additive virginiamycin is used to control *Streptococcus* spp. The vaccine is prepared by combining washed bacteria of the isolate *Selenomonas ruminantium* (SRR1) (between $10^7$ and $10^{11}$ cells/ml) and 1 ml of the adjvuant DEAE-Dextran. This is injected intramuscularly into dairy cattle prior to calving in order to develop antibodies against *Selenomonas ruminantium* lactic acid producing bacteria. The feed additive virginiamycin is included in the concentrate feed to provide between 150 and 450 mg per head per day.

Example 4

Pigs are often fed diets containing high concentrations of starch and some of this starch can pass undigested to the hind gut where it undergoes rapid fermentation leading to the accumulation of tactic acid. The adverse effects of lactic acid accumulation and low pH in the hind gut of pigs includes metabolic acidosis, compromised integrity of the gut wall and increased pathogenicity of gut organisms. Piglets can be treated against this condition by immunising them against *Prevotella*-like bacteria such as LAB01/07-3, or *Clostridium*-like *vitulinus* and can be further protected by the inclusion of an antibiotic feed additive in the diet such as virginiamycin.

Example 5

Dogs and cats have evolved as carnivorous species but are not fed diets containing processed cereal grain. The carbohydrate fraction of the diet is poorly digested in the small intestine of these animals. Undigested carbohydrate passing from the small intestine to the hind gut is rapidly fermented and result in accumulation of acid. The accumulation of acid and the subsequent adverse side effects can be prevented by vaccination against *Prevotella*-like (LAB03/D35). *Enterococcus*-like (LAB05/D23), *Clostridium*-like and/or *Selenomonas ruminantium*. Further protection against lactic acid production by *Streptococcus* spp. can be achieved using virginiamycin or similar type of Gram-positive antibiotic compound in the feed.

Example 6

Horses grazing lush green feed and/or supplemented with cereal grains are at risk of incomplete carbohydrates digestion in the small intestine and fermentative lactic acid accumulation in the hind gut. Acid accumulation in the gut can result in laminitis an development of adverse behaviour. The risk of these potential problems can be reduced by immunisation against *Streptococcus equinus* and the strategic use of antibiotics active against *Clostridium*-like *virtulinus* and *Selenomonas ruminantium*.

Example 7

Humans suffering from lactose intolerance, irritable bowel syndrome, or any side effects of acidic gut syndrome can be immunised against *Clostridium*-like *virtulinus* and/or *Selenomonas ruminantium* and treated strategically with antibiotics such as virginiamycin and problocks such as *Megasphera elsdeni,i Bifidabacteria,* Lu12 or Su109.

Example 8

1. Seroconversion in sheep vaccinated with bacterin comprised of formalin-killed lactic acid producing bacteria.

An experiment was conducted to examine whether sheep would raise antibodies in response to a range of bacterins comprising bacteria that are commensal organisms in the gatrointestinal tract of ruminants or horses.

Materials and Methods

Forty nine adult Merino whether( approximately three years of age were checked for uniformity and physical appearance before entering the study. All animals were weighed and treated against internal parasites (ivermectin) approximately 3 weeks before being randomly assigned to one of seven experimental groups (seven animals per treatment group). Each animal received a different vaccination treatment consisting of one of the bacterins described in Table 8.1 and animals in the control group received adjuvant only. All of the sheep remained at pressure for 34 weeks before being housed for a grain challenge experiment. During the grazing phase of the experiment the sheep were given access to good quality green pasture whenever possible.

TABLE 8.1

Details of microorganisms used in vaccine preparation

| | Microbe | Expt. ID code | Accession No. | Date of Deposit |
|---|---|---|---|---|
| 1. | *Streptococcus bovis* | Sb5 | N94/8255 | Mar. 8, 1994 |
| 2 | *Streptococcus bovis* | A2 | NM99/04455 | Jun. 24, 1999 |
| 3 | *Streptococcus equinus* | Seq | NM99/04457 | Jun. 24, 1999 |
| 4 | *Clostridium*-like *vitulinus* | LV | NM99/04462 | Jun. 24, 1999 |
| 5 | *Selenomonas ruminantium* | SR1 | NM99/04458 | Jun. 24, 1999 |
| 6 | *Selenomonas ruminantium* | SR2 | NM99/04460 | Jun. 24, 1999 |

Preparation of vaccines: Frozen isolates of all bacteria were thawed then cultured in BM 10 for between 6 and 10 hours. All incubation were at 37° C. Formalin was added to the incubation flasks to achieve a final concentration of 0.5% in the final solution. The cells ere then harvested by centrifugation and washed 3 times using sterile PBS before being made to final volume in PBS with a concentration of $5 \times 10^9$ cells/ml.

The vaccines were prepared by mixing equal volumes of the bacterial suspension and Freund's complete adjuvant in the case of the primary vaccinations and Freund's incomplete adjuvant for booster injections. The control animals received sterile PBS and adjvuant. Even vaccination injection was 2 ml administered intramuscularly. For the primary and secondary vaccination, each sheep received 4 injections, one in each shoulder and 1 into each of the semi-membranosa muscles of each hind leg. The booster given in the 35$^{th}$ week after the primary injection was only administered to the two hind legs.

Samples of blood were taken according to the schedule in Table 8.2 for measurements of antibodies against the bacteria use to vaccinate each treatment group. Development of ELISA methods for measurement of relevant antibody titres was an important component of this study and is described below.

ELISA protocol: Bacterial antigen was prepared in the same way as described for the immunisations, and stored in aliquots at −20° C. Optimal antigen dilution was found to be 1:260 (diluted in carbonate buffer); 100 μl of this suspension was added to each well of ELISA plates (Immunolon II flat bottom 96-well plates). Plates were then covered and incubated overnight at 4° C. Antigen was removed from the wells and the plates washed 3 times in PBST (NaCl & 8 g, Na2HPO4 1.15 g, KH2PO4 0.2 g, 0.5 ml Tween 20, in 1000 ml MQ water, pH 7.2–7.4) using an automated plate washer (TiterTek Microplate Washer 120, Flow Laboratories. Blocking buffer (1% Bovine serum albumin (Sigma) in PBST) was added to each well and allowed to incubate at 37° C. for 1 hour, followed by 3 washes and PBST. Titrations of the test sera were performed and optimal dilutions for a standard assay determined. Test sera were analysed by diluting sera in blocking buffer at levels found to be optimal for each antigen. Following dilution 100 μl of each test serum was analysed in duplicate wells; in addition, prevaccination serum was always included in each plate. Negative controls (PBS) and standards were included in triplicate. Standard were prepared by double serial dilution (in blocking buffer) starting at 1:100 of previously-assayed sheep sera known to contain Sb5 antibodies. After adding the serum samples, plates were incubated for 1 hour at 37° C. followed by 3 washes in PBST. The optimal dilution of the horseradish peroxidase conjugates was found to be 1:1,000 for the sheep (rabbit anti-shape-IgG (H & L) HRP, BioRad),. Conjugates were diluted accordingly in blocking buffer, 100 μl added to appropriate wells, and the plates incubated for 1 hour at 37° C. Plates were again washed 3 times with PBST, and 100 μl of substrate added (34 mg o-phenylenediamne in 100 ml citriate phosphate buffer (light sensitive), 50 μl of 30% $H_2O_2$ (added just prior use) (citrate phosphate buffer: citric acid 7.3 g. $Na_2HPO_4$ 9.5 g, 800 ml MQ water, pH to 6 with 10 M NaOH and brought to 1000 ml). Plates were incubated in the dark at room temperature for 30 mins at which time the enzymatic reaction was stopped by the addition of 100 μl of 2N sulphuric acid. Absorbances were read in a microplate reader (Benchmark, BioRad) and the data analysed using Microplate Manager/PC 4.0 (BioRad) software. Analysis parameters and standard curve information were included for each plate.

Samples of rumen fluid were taken via stomach tube and pH was measured before taking a sub-sample for determination of potential lactic acid production. The remainder of the sample was acidified for later measurement of volatile fatty acid concentrations. Potential lactic acid production was measured by incubating 4 ml of rumen fluid with 1 ml glucose solution containing 50 mg glucose/ml. Following incubation with glucose for 20 hours pH was measured before acidification with 0.1 ml of concentrated sulphuric acid and frozen for subsequent analysis of lactic acid concentration.

TABLE 8.2

Schedule of immunisation and sampling to monitor systemic antbody levels and the consequences of vaccination in Example 8

| Week | Procedure |
| --- | --- |
| −1 | Blood sample (First pro-bleed) |
| 0 | Blood sample (Second pre-bleed) + primary immunisation |
| 2 | Blood sample for antibody measurement |
| 4 | Blood sample + secondary (first booster) immunisation |
| 6 | Blood sample + collect rumen fluid and faeces |
| 8 | Blood sample |
| 10 | Blood sample + collect rumen fluid and faeces |
| 12 | Blood sample |
| 14 | Blood sample |

For bacterial enumeration a rumen fluid samples were processed following the one-hour exposure method prior to incubation of Yanke and Cheng (1998). The rumen fluid was serially diluted ten-fold in anaerobic dilution solution (ADS) (Caldwell and Bryant, 1966) to a final dilution of $10^{-8}$. Three dilutions ($10^{-6}$, $10^{-7}$ and $10^{-8}$) were used to inoculate the media roll tubes in triplicate for each dilution. A modified semi-selective MRS-Agar medium, Oxoid, England (de Man et al., 1960) was used to culture the lactic acid bacteria was the pH of the medium adjusted to 5.5. The tubes were incubated at 39° C. for three days. Faecal samples collected directly from the rectum were mixed with two times their weight of distilled water. 4 ml of the slurry was incubated with glucose solution as described for rumen fluid potential lactic acid measurement. A further quantity (approx 10 ml) was filtered through 4 layers of cheese cloth before measuring pH and then acidifying the sample for later analysis of volatile fatty acids.

VFA concentrations measured by gas chromatography (Hewlett-Packard) and L(+)lactam and D(−) lactate analyzed by auto-analyzer (Cobas Mira Autoanalyser, Roche Diagnostics Inc., French Forest, NSW) using an enzymatic procedure (Stat-Pak™ Rapid Lactate Test, Behring Diagnostic Inc., Somerville, N.J.)

Results

There were good levels of seroconversion (Table 8.3) in response to the various bacteria used in this experiment and elevated antibody titres persisted to week 14 following the primary vaccination.

TABLE 8.3

Antibody titres (Ab units × 1000) measured in serum from sheep immunised with different bacterin. Time in weeks refers to weeks after the primary vaccination. All sheep were re-immumised 4 weeks after the primary vaccination. Streptococcus bovis; Streptococcus equinus; Clostridium-like vitulinus; Selenomonas ruminantium isolates R1 and R2 respectively

| Group | Sheep | Bacterin | Pre vacc'n | Week 2 | Week 4 | Week 6 | Week 8 | Week 10 | Week 12 | Week 14 |
|---|---|---|---|---|---|---|---|---|---|---|
| 1 | 1 | S. bovis Sb5 | 0 | 0 | 0 | 240 | 0 | 166 | 271 | 807 |
| 1 | 3 | S. bovis Sb5 | 0 | 0 | 0 | 0 | 0 | 0 | 0 | 295 |
| 1 | 5 | S. bovis Sb5 | 0 | 0 | 0 | 462 | 224 | 700 | 381 | 0 |
| 1 | 6 | S. bovis Sb5 | 0 | 114 | 183 | 557 | 224 | 370 | 403 | 386 |
| 1 | 7 | S. bovis Sb5 | 88 | 178 | 296 | 1,136 | 620 | 490 | 588 | 538 |
| 2 | 8 | S. bovis A2 | 0 | 28 | 70 | 311 | 100 | 294 | 712 | 528 |
| 2 | 9 | S. bovis A2 | 0 | 0 | 25 | 181 | 116 | 232 | 2,714 | 712 |
| 2 | 10 | S. bovis A2 | 11 | 14 | 37 | 181 | 218 | 187 | 1,094 | 498 |
| 2 | 11 | S. bovis A2 | 0 | 8 | 25 | 121 | 175 | 329 | 3,567 | 3,567 |
| 2 | 12 | S. bovis A2 | 9 | 24 | 25 | 120 | 81 | 79 | 1,823 | 1,321 |
| 2 | 13 | S. bovis A2 | 6 | 11 | 15 | 64 | 99 | 110 | 1,823 | 2,904 |
| 2 | 14 | S. bovis A2 | 12 | 33 | 44 | 197 | 227 | 180 | 3,567 | 2,220 |
| 3 | 15 | S. equinus | 9 | 22 | 85 | 105,000 | 2,011 | 5,197 | 10,140 | 5,622 |
| 3 | 16 | S. equinus | 10 | 11 | 20 | 302 | 80 | 38 | 23 | 18 |
| 3 | 17 | S. equinus | 8 | 9 | 11 | 484 | 558 | 871 | 3,657 | 3,936 |
| 3 | 18 | S. equinus | 9 | 28 | 123 | 300,000 | 18,710 | 27,010 | 265,900 | 73,440 |
| 3 | 19 | S. equinus | 9 | 28 | 161 | 6,567 | 4,430 | 971 | 385 | 784 |
| 3 | 20 | S. equinus | 9 | 20 | 53 | 2,225 | 191 | 824 | 501 | 1,250 |
| 3 | 21 | S. equinus | 9 | 13 | 35 | 797 | 109 | 90 | 67 | 101 |
| 4 | 22 | C. vitulinus | 13 | 206 | 98 | 883 | 477 | 899 | 324 | 1,221 |
| 4 | 23 | C. vitulinus | 33 | 115 | 142 | 394 | 244 | 265 | 100 | 89 |
| 4 | 24 | C. vitulinus | 1,014 | 202 | 265 | 103 | 130 | 43 | 45 | 554 |
| 4 | 25 | C. vitulinus | 127 | 145 | 365 | 1,181 | 477 | 394 | 365 | 159 |
| 4 | 26 | C. vitulinus | 0 | 0 | 313 | 2,948 | 243 | 634 | 313 | 234 |
| 4 | 27 | C. vitulinus | 0 | 483 | 292 | 1,944 | 668 | 1,197 | 2,898 | 1,446 |
| 4 | 28 | C. vitulinus | 0 | 243 | 417 | 123 | 469 | 602 | 243 | 0 |
| 5 | 29 | SR R1 | 17 | 125 | 120 | 181 | 246 | 1,346 | 829 | 688 |
| 5 | 30 | SR R1 | 16 | 446 | 172 | 229 | 303 | 392 | 441 | 396 |
| 5 | 31 | SR R1 | 2 | 261 | 300 | 261 | 114 | 89 | 648 | 441 |
| 5 | 32 | SR R1 | 15 | 145 | 115 | 545 | 16,130 | 5,058 | 40,660 | 24,140 |
| 5 | 33 | SR R1 | 21 | 159 | 124 | 241 | 145 | 124 | 127 | 92 |
| 5 | 34 | SR R1 | 0 | 55 | 46 | 132 | 132 | 67 | 86 | 83 |
| 5 | 35 | SR R1 | 0 | 83 | 67 | 109 | 94 | 170 | 384 | 563 |
| 6 | 36 | Sr R2 | 0 | 117 | 3,292 | 3,403 | 2,570 | 9,975 | 4,367 | 3,132 |
| 6 | 37 | Sr R2 | 7 | 14 | 49 | 110 | 261 | 227 | 249 | 351 |
| 6 | 38 | Sr R2 | 6 | 12 | 63 | 329 | 619 | 430 | 1,156 | 512 |
| 6 | 39 | Sr R2 | 6 | 51 | 110 | 210 | 169 | 261 | 437 | 1,450 |
| 6 | 40 | Sr R2 | 8 | 23 | 78 | 723 | 913 | 12,000 | 3,240 | 1,174 |
| 6 | 41 | Sr R2 | 10 | 19 | 72 | 107 | 185 | 322 | 88 | 124 |
| 6 | 42 | Sr R2 | 8 | 30 | 2,255 | 11,940 | 432 | 235 | 214 | 442 |

During the period that sheep were grazing spring and summer pastures there was no significant effect of vaccination treatment on faecal dry matter content, as an index of faecal consistency and diarrhoea (see Table 8.4). Although not statistically significant there were more lactic acid bacteria (growing on MRS medium) to the rumen fluid of sheep immunized against the S. ruminantium bacteria. This is an important result and is consistent with the pH of rumen fluid shown in Table 8.5 (week 10) and Table 8.6 (week 38) where the treatment groups with highest numbers of lactic acid producers were found to have lowest pH.

TABLE 8.4

Body weight of sheep at week 34 and the faecal dry matter % measured during weeks.

| | Body weight (Week 34) | Body weight Week 34 SE | Faecal dry matter (Week 0) | Faecal DM Week 0 SE | Faecal dry matter (Weeks 6 & 10) | Faecal DM Weeks 6 & 10 SE |
|---|---|---|---|---|---|---|
| Sb5 | 56.2 | 2.87 | 23.7 | 1.86 | 25.0 | 1.617 |
| A2 | 52.9 | 2.42 | 21.4 | 1.93 | 22.5 | 1.810 |
| Seq | 54.0 | 0.75 | 23.8 | 2.69 | 22.1 | 1.760 |
| LV | 56.0 | 1.54 | 22.4 | 1.36 | 22.3 | 1.803 |
| SR1 | 54.4 | 1.83 | 24.8 | 1.36 | 22.5 | 1.803 |
| SR2 | 56.3 | 1.83 | 24.7 | 2.13 | 24.2 | 1.393 |
| Control | 56.3 | 1.44 | 26.4 | 2.63 | 22.6 | 0.998 |

TABLE 8.5

Rumen and faecal pH and the pH following incubation with glucose in samples taken from vaccinated sheep 6 and 10 weeks following vaccination with a range of lactic acid-producing bacterins. Numbers of bacterias (cells/ml) measured in the rumen fluid during week 10.

| | Rumen pH | SE | Faecal pH | SE | Total bacteria × $10^8$ | Lactic acid bacteria × $10^7$ | Lactic acid bacteria % of total |
|---|---|---|---|---|---|---|---|
| Sb5 | 7.0 | 0.075 | 7.7 | 0.77 | 10.1 | 8.3 | 9.1 |
| A2 | 7.0 | 0.075 | 7.4 | 0.77 | 1.5 | 9.2 | 6.2 |
| S.Eq | 6.9 | 0.075 | 7.6 | 0.77 | 1.3 | 6.7 | 5.4 |
| LV | 7.0 | 0.075 | 7.6 | 0.77 | 1.3 | 6.8 | 5.7 |
| SR R1 | 6.9 | 0.075 | 7.7 | 0.77 | 2.1 | 46.5 | 12.7 |
| SR R2 | 6.9 | 0.075 | 7.5 | 0.77 | 2.8 | 22.0 | 6.3 |
| Control | 6.9 | 0.078 | 4.5 | 0.80 | 1.3 | 11.9 | 7.9 |

2. Response to grain acidosis challenge in sheep 38 weeks after initial immunisation Thirty four weeks after the primary vaccination all sheep were brought into the animal house where they were weighted and housed in individual pens with free access to clean water. All animals were treated with a broad-spectrum anthelmintic. For a period of four weeks animals were fed a mixture of cereal & lucerne chaff (1100 g/d).

Five days after entering the shed sheep were re-vaccinated as described above and were given approximately 60 g wheat/d together with 1100 g chaff. During week 37 (post primary vaccination) samples of rumen fluid and faeces were taken for measurement of pH and potential lactate production. Portion of the samples were also taken for later analysis of volatile fatty acids.

Grain challenge and sampling: On day 1 of the challenge, 1 kg of whole wheat was offered to each sheep at approximately 7 AM. For those sheep that had not eaten all the wheat within 2 hours an amount of cracked wheat, equivalent to the residue and was administered into the rumen via stomach tube as a slurry made up with water. Immediately after administration of the wheat, blood samples were taken for antibody measurements and for haptoglobin determination. Approximately eight hours after first feeding the wheat (4 PM), samples of rumen fluid were taken for measurement of pH, VFA and lactate.

On the following morning a rumen sample was taken for measurement of pH, VFA and lactate and a check made of faecal consistency (faecal scores). Faecal samples were collected for measurement of pH and dry matter. All sheep were then offered 500 g wheat and 1 hour later refusals weighed. An amount of cracked wheat equivalent to the residue and administered into the rumen via a stomach tube. Chaffed lucerne and cereal hay was fed ad libitum after the final dose of wheat and intakes were measured daily. Samples of rumen fluid were taken 8 hour later (32 h from first wheat) and faeces were scored for consistency and sampled for pH. Forty eight hours after first offering wheat to the sheep of a final rumen sample was taken and faecal scores were recorded. A sample of blood was taken for haptoglobin analysis.

Antibody levels, rumen pH and the potential lactic acid production measured during week 38 after primary challenge (4 weeks after the second booster injection administered during week 34) are summarised in Table 8.6. The major finding is that the rumen pH pre-grain challenge and on "normal" feed was significantly (P<0.001) affected by vaccination treatment. The control animals had the highest level of acid and the group vaccinated with Sb A2 had the lowest acidity (highest pH). These data strongly suggest an affect on vaccination on acid production during rumen fermentation on normal diets.

In vivo responses to the "intake" of excessive levels of wheat are summarised in Table 8.7. There were significance (P<0.01) differences in rumen lactic acid concentrations with the sheep vaccinated with Sb A2, vitulinus (LV) and SR2 having the lowest concentrations of lactic acid in the rumen.

Faecal consistency scores were significantly (p<0.01) different in sheep vaccinated with different antigens. The sheep vaccinated against *S. equinus* consistency had more diarrhoea than the other treatment groups and these sheep also had the lowest feed intake.

TABLE 8.6

Antibody titres (Ab units × 1000) at week 38, rumen fluid pH and potential lactate production measured in rumen fluid and faeces.

| Treatment | Antibody titre Week 38 | Rumen fluid pH Week 38 | Potential lactate Rumen Week 38 | Potential lactate Faeces Week 38 |
|---|---|---|---|---|
| Sb5 | 260 | 7.02 | 27.3 | 18.9 |
| A2 | 30 | 7.09 | 19.1 | 25.2 |
| Seq | 15 | 6.95 | 18.6 | 24.7 |
| LV | 3492 | 6.90 | 16.8 | 19.7 |
| SR1 | 496 | 6.75 | 23.4 | 28.8 |
| SR2 | 690 | 6.82 | 13.6 | 19.1 |
| control | 0* | 6.89 | 30.6 | 27.2 |
| Sig | 0.001 | 0.001 | NS | NS |
| SE | 314 | 0.078 | 6.0 | 3.5 |

*Animals in the control group and antibodies against LV at a level <2% of the group vaccinated against LV, and no antibodies against other antigens used in this experiment.

TABLE 8.7

Responses in vaccinated sheep to grain acidosis challenge. Faecal consistency score were based on 1 = normal pelleted faeces and 5 = diarrhoea. Feed intake values are: g/d.

| Treatment | Rumen lactate (32 h after wheat) | Rumen pH (32 h after wheat) | Faecal pH (24 h after wheat) | Average faecal score 24 to 48 h after first wheat | Average feed intake for 72 h after first wheat |
|---|---|---|---|---|---|
| Sb5 | 25.5 | 5.81 | 6.51 | 1.73 | 674 |
| A2 | 0.6 | 5.99 | 5.54 | 3.31 | 639 |
| Seq | 56.3 | 5.65 | 5.90 | 3.73 | 516 |
| LV | 0.0 | 5.91 | 5.48 | 2.77 | 599 |
| SR1 | 19.3 | 5.83 | 6.19 | 2.25 | 665 |
| SR2 | 2.1 | 5.83 | 5.67 | 3.39 | 697 |
| Control | 0.1 | 6.16 | 5.75 | 2.31 | 786 |
| Sig | 0.01 | NS | NS | 0.01 | NS |
| SE | 12.7 | 2.1 | 0.45 | 0.38 | 69 |

Discussion

The results of this study have shown that it is possible to immunise sheep against aggressive lactic acid producing bacteria that normally inhabit the gastrointestinal tract and that by producing antibodies to these lactic acid producing bacteria the animal is able to alter the response to dietary carbohydrate overload. Changes in response to the grain overload challenge include reduced amounts of rumen lactic acid accumulation in sheep vaccinated with A2. SR2 and Cv. Sheep in these treatment groups had the lowest levels of lactic acid of the vaccinated sheep. The treatment group with the highest rumen lactic acid (*S. equinus*) had the lowest subsequent feed intake and the most server diarrhoea.

It is concluded that lactic acid bacteria other than Sb 5 can be used as antigens to alter the animals ability to respond to fermentative acidosis challenge and that other bacteria such as A2, Cv and SR2 may actually be more effective antigens in preparing the animal to control lactic acid build up in the rumen following a carbohydrate challenge. The only bacterial antigen used in this study that was not isolated from a ruminant animal (*S. equinus*, isolated from a horse) had the least effect in reducing lactic acid accumulation. This indicates the importance of discovering and isolating the lactic acid producing bacteria specifically associated with type of animal and relevant diet.

Example 9

Isolation of Predominant and Aggressive Lactic Acid Producing Bacteria from the Digestive Tract of Pigs, Dogs and Humans The lactic acid producing bacteria in the hind gut or large bowel (caecum, colon and rectum) of different vertebrate species vary depending on the substrate available for fermentation and the rate of turnover of digesta in the large bowel as this determines average residence time of bacteria in the large bowel. The amount and nature of substrate entering the large bowel is determined by two major factors: diet and the pre-digestion of dietary substrates in the stomach and small intestine prior to passage of digesta into the large bowel. Pre-digestion in the stomach and small intestine are, in turn, are influenced by the nature and efficiency of digestive enzymes (such as amylase, amyloglucosidase, pepsin, pepsinogen, brush—borer carbohydrate degrading enzyme), rate of intake and effective of chewing and particle size diminution such as occurs in the crop of bird, the rate of digesta passage (determined by factors such as animal species, meal size, level of stress) and the absorptive capacity of the digestive tract. The rate of turnover of digesta in the large bowel is determined by the size of compartments such as the caecum and colon relative to the flow of digests through the compartments. The half-time for digesta residence in different animal species can vary from days to just several hours. Variation in residence time and the amount and nature of substrate available for fermentation in different vertebrate species, consuming different diets, therefore means that there will be important differences in the dominant lactic acid producing bacteria that colonise the large bowel.

Even in situations where it is well known that a species of bacteria such as the lactobilli or streptococci produce lactic acid it is essential to discover and isolate the actual strains of that genus specifically capable of surviving in the particular digestive compartment under the prevailing conditions of flow and substrate availability with the ability to compete with other gut bacteria. Moreover it is essential to identify and select the strain(s) numerically important and capable of abundant lactic acid production. The experiments described below were designed to discover and isolate the predominant lactic acid producing bacteria from the digestive tract of pigs, dogs and humans. Since there are no major physiological changes in the pH, temperature or anaerobic/aerobic status of digesta during passage from the caecum through the colon and rectum, samples of faeces were considered to provide suitable material for isolating the lactic acid bacteria of the large bowel of the respective vertebrate species.

(i) Discovery and isolation of lactic acid producing bacteria from pigs

Commercial diets for pig production are commonly based on cereal grain. The grain is normally processed by grinding through a hammer mill before mixing with protein, vitamins and minerals to form a complete diet. In the current study samples of faeces were taken from 5 pigs in a commercial piggery. The pigs weighing around 40 kg and 6 weeks of age were housed in group pens and were considered to be in good health with no signs of abnormality at the time of sampling. The diet contained barley and sorghum (50:50 by weight) as the source of grain and was formulated to contain 14% protein. The level of feeding was designated to be ad libitum and was offered to the animals twice per day.

Faeces were prepared as described in Example 1 for the discovery and isolation of the most numerous species/strains of lactic acid bacteria. The process of selecting colonies for dominance and lactic acid production and isolating pure strains involved enumeration of lactic acid strains on a modified semi selective MRS and growth in a broth of glucose based BM 10 as described in Example 1. Those isolates considered the most important lactic acid producers were studied microscopically for purity and gross morphological classification.

There were 2 isolates considered to be different from lactic acid producing microbes isolated in our previous presearch. These isolates are described in Table 9.1 and have been deposited with the Australian Government Analytical Laboratories (AGAL). Dates and accession numbers are summarised in Table 9.1

TABLE 9.1

Details of two lactic acid-producing producing bacterial isolates discovered in the faeces of pigs under commercial piggery conditions.

| Lab code number | LAB 01/07-3 | LAB 02/11-2 |
| --- | --- | --- |
| Description | Short rods arranged in short chains and filaments, Gram+ | Short straight rods with round ends, also long thin rods |
| Preliminary classification | *Prevotella*-like | non-slime producing lactic acid bacterial isolates |
| AGAL accession number | NMOO/12630 | NM00/12631 |
| Date of AGAL deposition | Jun. 29, 2000 | Jun. 29, 2000 |

(ii) Discovery and isolation of lactic acid producing bacteria from dogs

Two experiments were undertaken to identify the most important lactic acid bacteria in the large bowel of dogs on a high carbohydrate dies fed with, or without, the antibiotic feed additive virginiamycin. As indicated in Example 1 there are situations where the antibiotic feed additive virginiamycin produces incomplete control over lactic acid accumulation in the digestive tract of ruminant animals. The experiment outlined below was undertaken to determine the level of control of virginiamycin over lactic acid accumulation in the large bowel of dogs. The second experiment in this Example 9 was designed to discover and isolate the dominant lactic acid, producing bacteria from the faeces of dogs fed the same diet either with or without virginiamycin.

1. Dose virginiamycin control lactic acid production in the large bowel of dogs?

The main objective of this trial was to investigate various doses of virginiamycin in terms of its effect on faecal consistency and hind gut fermentation.

Design: There were 4 treatment groups consisting of unmedicated control, and virginiamycin at 3 levels: 0.25, 0.5 and 1 mg/kg body weight. Dogs were acclimatised to a diet based on the tinned 'No Frills' dog food for approximately 2 weeks prior to a seven-day treatment period in which fructo-oligosaccharide raftilose was added to the diet at a rate of 3.5 g/kg metabolic body weight. There were five dogs per treatment.

Measurements were made of faecal pH, dry matter, consistency and chemical assays were conducted to measure VFA, D-lactic acid and L-lactic acid.

Results The main results are summarised in Table 9.2.

The effect of raftilose inclusion is to reduce pH by approximately 1 unit. The secondary effects associated has an overriding effect on pH and masks the potential beneficial effects of reduced D-lactic acid associated with the inclusion of virginiamycin. The observation that virginiamycin reduced D-lactic acid but had to little effect on L-lactic confirms that virginiamycin does not always inhibit all lactic acid bacteria.

2. Discovery and isolation of lactic acid bacteria from dogs

Two dogs were fed a commercial dry dog food for 4 weeks before and then during the experimental period. Virginiamycin (Eskalin 20) was added to the diet of one dog for a period of 7 days prior to faecal sampling to provide 0.5 mg/kg body weight. Samples of faeces were taken for the analysis of pH and lactic acid concentrations at the same time as those taken for isolation of lactic acid producing bacteria.

Isolation and purification of the lactic acid bacteria was achieved using the methods previously described in Example 1. Two lactic acid bacteria were isolated from the dog not treated with virginiamycin and a further two from the dog treated with virginiamycin (see Table 9.3)

TABLE 9.3

Characteristics of faeces and details of the lactic acid producing bacteria isolated from dogs.

| | Control (no virginiamycin) "M" | | Virginiamycin "T" | |
|---|---|---|---|---|
| L(+)Lactate | 2.55 mmol/L | | 0.34 mmol/L | |
| D(−)Lactate | 2.06 mmol/L | | 0.45 mmol/L | |
| Faecal pH | 5.49 | | 5.34 | |
| Lab code No. | LAB 03/D35 | LAB 04/D37 | LAB 05/D23 | LAB 06/D29 |
| Description | Predominantly rods in filaments. (Gram+) | Predominantly large cocci, occurring mainly in pairs and singly (larger than the S. bovis isolates SB R1 (Gram+) | Predominantly small cocci < than 1 $\mu$m in diameter mainly as diplococci (Gram+) | Long > than 5 $\mu$m thick rods, in singles and short chains. |
| Preliminary classification | Prevotella-like | Streptococcus-like | Enterocossus-like | Non-slime producing lactic acid isolate |
| Accession No. | NM00/12632 | NM00/12633 | NM00/12634 | NM00/12635 |
| Despot date | Jun. 29, 2000 | Jun. 29, 2000 | Jun. 29, 2000 | Jun. 29, 2000 | with the increased acidity include more sloppy consistency, reduced dry matter and increased lactic acid.

There was little effect of the virginiamycin on the pH, faecal consistency, dry matter content and VFA concentrations. The only clear effect of virginiamycin in this experiment was to reduce the concentration of d-lactic acid. Virginiamycin had this effect on the lactic acid at all levels of inclusion.

TABLE 9.2

Summary of faecal pH and lactic acid concentrations in dogs fed a diet of tinned "No Frills" dogs food and added raftilose. A consistency score of 5 = firm, normal faeces and 1 = diarrhoea

| | Pre-Raftilose (mean all dogs) | Control No VM | VM 0.25 | VM 0.5 | VM 1.0 | Treat signif |
|---|---|---|---|---|---|---|
| pH | 6.0 | 5.4 | 5.2 | 4.9 | 4.9 | |
| Consistency | 5.0 | 3.4 | 3.6 | 3.7 | 3.8 | |
| Dry matter | 25.0 | 20.5 | 22.0 | 22.5 | 24.2 | |
| L-lactic | 0.6 | 11.5 | 2.2 | 13.8 | 11.8 | |
| D-lactic | 0.1 | 8.3 | 0.2 | 0.4 | 0.3 | ** |
| Total VFA | 88.0 | 80.0 | 80.5 | 93.7 | 73.5 | |

Discussion: There were high concentrations of VFA in all treatment groups irrespective of whether or not raftilose was included in the diet. It is likely that this high level of VFA An experiment was conducted to discover and isolate the most important lactic acid producing bacteria from the large bowel of a human subject in good health and consuming a normal balanced diet with a range of different sources of carbohydrate (bread, pasta, rice and potato), various sources of protein (plant and animal origin) and a range of fruit and vegetables providing soluble and insoluble non-starch polysaccharides. The methods used to isolate the most important lactic acid bacteria were as described in Example 1.

The pH of the faecal sample was 6.5 and there were very low levels of lactic acid (1.0 mmol/kg L(+) lactate). Descriptions of the two dominant lactic acid producing isolates are given in Table 9.4 together with details of the AGAL lodgement.

TABLE 9.4

Description of lactic acid producing bacterial isolates from human faeces

| Lab code of lactic acid isolate | LAB 07/H1 | LAB 08/H15 |
|---|---|---|
| Description | Predominantly short rods forming filaments | Endospore-forming bacteria, rod shaped, |

TABLE 9.4-continued

Description of lactic acid producing bacterial isolates from human faeces

| Lab code of lactic acid isolate | LAB 07/H1 | LAB 08/H15 |
|---|---|---|
| Preliminary classification | Bacteriodes-like | straight with spores. (Gram+) Non-slime producing lactic acid isolate |
| AGAL accession No. | NM00/12636 | NM00/12637 |
| Date of AGAL deposition | Jun. 29, 2000 | Jun. 29, 2000 |

Example 10

Isolation of Lactic Acid Producing Bacteria from the Stomach

While most lactic acid production as a result of fermentation of carbohydrate takes place in the large bowel or hind gut it is also possible for fermentation and acid accumulation to occur in the stomach of some vertebrate species. Acid accumulation in the stomach can be important in development of ulcers in the stomach. While acidic damage is typically considered to be a result of acid secreted by the stomach. It is generally considered that the true stomach of monogastric animals and humans is too acidic (around pH 2) for growth and persistence of most bacterial species. It is certainly not considered that bacterial fermentation in the stomach contributes to the acid load in that digestive compartment. However there are non-acid secreting regions in the stomach of most monogastric animal and it is in these parts that lactic acid producing bacteria to survive. In some vertebrates, including the horse, feed can be held in the stomach for several hours. Under these conditions it is possible that bacteria capable of surviving acidic conditions while fermenting carbohydrate may contribute to the acid load in the stomach.

An experiment was conducted to determine if lactic acid bacteria occur the stomach of a horse consuming grain. A horse was fed a diet consisting of pasture and 2 kg/d of ground wheat grain for 2 weeks before it was humanely killed. Contents of the stomach were removed and sampled for isolation of dominant lactic acid producing bacteria using methods described in Example 1.

A mixed culture of lactic acid bacteria was discovered and isolated from the stomach contents. There were numerous colonies even at $10^{-8}$ dilution and lactic acid production was predominantly L(+) lactate. The purification of individual strains has not yet been completed.

The results of this experiment show that lactic acid producing bacteria in the stomach of monogastric animals other than horses may have an important role in contributing to the acid load in the stomach that is responsible for ulcer formation in a wide range of intensively fed and managed domestic animals as well as humans. Isolation of these strains, using the methods described in Example 1, is likely to yield strains of lactic acid bacteria with important roles in vaccine preparation, diagnostic methods and developing pharmaceutical preparations.

Example 11

Vaccination of Horses with the Combination of S. bovis (Sb R1 A2) and Streptococcus equinus (SE R2)

Seven horses grazing senescent winter pastures were treated against internal parasites using a broad spectrum ivermectin drench three weeks before the start of the experiment. At the start of the experiment three of the horse were vaccinated against the lactic acid producing bacteria: *S. bovis* (strain Sb R1-A2) and *S. equinus* (strain SE R2). Three weeks after the primary vaccination the secondary vaccination was administered. Samples of blood and faeces were taken prior to vaccination, at the time of the secondary vaccination and again 2 weeks later.

Vaccine preparation and procedure: Pure isolation of *S. bovis* and *S. equinus* were thawed and cultured in Basal Medium 10 at 37°. Formalin was added to the cultures at the end of the growth phase to achieve a final concentration of 0.5%. The cells were harvested by centrifugation at 17,000 g for 20 minutes. The supernatant was discarded before re-suspending the cells in sterile PBS followed by centrifugation. The cells were washed 3 times in this way before being counted and made to a final volume in sterile PBS containing $1 \times 10^{10}$ cells/ml. Prior to vaccination equal volumes of each bacterial suspension were mixed. The mixed bacterial suspension was then combined with aluminum hydroxide adjuvant (Alhydrogel 1.3%) in equal volume. The vaccine was administered subcutaneously on the neck of each horse (2 ml per injection with $5 \times 10^9$ cells of each bacteria per injection). Following each injection horses were regularly checked for any side effects of the vaccination and the injection site monitored by measurement.

Results: The site reaction to the vaccine was clearly observed in all horses and decreased in volume to around 10 ml within 48 h for the primary injection and 96 h for the secondary vaccination. No adverse side effects were observed during the period of monitoring following vaccination.

TABLE 11.1

Site reaction (volume in ml of subcutaneous oedema) following primary and secondary vaccination into the neck of horses with the dual bacterin Sb A2 and SE R2

| Horse ID | Primary vaccination | | Secondary vaccination | | |
|---|---|---|---|---|---|
| | 24 h | 48 h | 24 h | 48 h | 96 h |
| 1 | 12 | 12 | 59 | 36 | 9 |
| 2 | 54 | 15 | 90 | 20 | 9 |
| 3 | 5 | 5 | 56 | 6 | 6 |
| Average: | 23.7 | 10.7 | 68.2 | 20.5 | 8.0 |
| SE | 15.3 | 3.0 | 10.9 | 8.8 | 1.2 |

TABLE 11.2

Antibody levels (ELISA absorbance) against S. bovis (A2) and S. equinus in serum from vaccinated horses

| Horse ID | S. equinus (SE R2) | | | S. bovis (A2) | | |
|---|---|---|---|---|---|---|
| | Pre-vaccination | Week 3 | Week 5 | Pre-vaccination | Week 3 | Week 5 |
| 1 | 0.099 | 0.087 | 0.110 | 0.053 | 0.053 | 0.087 |
| 2 | 0.097 | 0.086 | 0.135 | 0.048 | 0.100 | 0.130 |
| 3 | 0.088 | 0.128 | 0.165 | 0.060 | 0.096 | 0.129 |
| Average: | 0.095 | 0.100 | 0.137 | 0.054 | 0.083 | 0.115 |
| SE | 0.003 | 0.014 | 0.016 | 0.003 | 0.015 | 0.014 |

There was good seroconversion and consistent antibody production against both bacterins in all horses (Table 11.2). The seroconversion and antibody levels measured in serum are consistent with the site reaction detailed in Table 11.1 and demonstrate efficacy of vaccination using dual lactic acid bacterins.

Conclusion: Multiple bacterin vaccines against lactic acid bacteria are effective in producing seroconversion and consistent antibody responses to both antigens.

INDUSTRIAL APPLICABILITY

The present invention makes use of a vaccine for the prevention of lactic acidosis in a vertebrate, said vaccine comprising at least one isolated microorganism, or fragment or fragments thereof, wherein said microorganism is capable of producing lactic acid within the gut of said vertebrate, and wherein said microorganism is selected from the group consisting of: *Clostridium*-like species, *Prevotella*-like species, *Bacteroides*-like species, *Enterococcus*-like species, *Selenomonas* species, non-dextran slime producing *Streptococcus* species and non-slime producing lactic acid bacterial isolates.

TABLE 1

Fermentation products of Streptococcus bovis, Streptococcus equinus, Clostridium-like vitulinus and Selenomonas ruminantium isolates in a broth of basal medium 10 with glucose (0.5%).

| Isolate | End products |
|---|---|
| Streptococcus bovis | L-Lactic+ |
| Streptococcus aqueous | L-Lactic |
| Clostridium-like vitulinus (LV R1, LV | D-Lactic |
| Clostridium-like vitulinus (LV R3) | L-Lactic, D-Lactic |
| Selenomonas ruminantium (SR R1) | L-Lactic Acetic, Propionic |
| Selenomonas ruminantium (SR R2) | L-Lactic, D-Lactic, Acetic, |
| Selenomonas ruminantium (SR R3) | L-Lactic, D-Lactic, Acetic, |

+Bold indicates main fermentation product.

TABLE 2

Fermentation of carbohydrate substrates by S. bovis, S. equinus, Clostridium-like vitulinus and S. ruminantium isolates from pasture-adapted sheep supplemented with wheat grain plus urea.

| | Bacterial Isolates | | | | | | | | | |
|---|---|---|---|---|---|---|---|---|---|---|
| | Streptococcus | | Clostridium-like vitulinus | | | | | S. riuninantium | | |
| Carbohydrate | B. bovis | S. equinus | LV R1 | LV R2 | LV R3 | LV R4 | LV R5 | SR R1 | SR R2 | SR R3 |
| Arabinose | − | − | − | − | − | − | − | − | − | − |
| Cellobiose | + | + | + | + | − | + | + | + | + | + |
| Fructose | + | + | + | + | + | + | + | + | + | + |
| Galactose | + | + | − | − | + | − | − | + | + | + |
| Glucose | + | + | + | + | + | + | + | + | + | + |
| Glycerol | − | − | − | − | − | − | − | − | − | − |
| Inulin | +* | − | + | + | − | + | + | − | − | − |
| Lactose | + | −** | − | − | + | − | − | + | + | + |
| Maltose | + | + | + | + | − | + | + | + | + | + |
| Mannitol | − | − | − | − | + | − | − | + | − | − |
| Mannose | + | + | + | + | + | + | + | + | + | + |
| Raffinose | + | + | + | + | + | + | + | + | + | + |
| Ribose | − | − | − | − | − | − | − | + | + | − |
| Sorbitol | − | − | − | − | − | − | − | + | + | − |
| Starch | + | − | − | − | − | − | − | − | + | + |
| Sucrose | + | + | + | + | + | + | + | + | + | + |
| Xylose | − | − | − | − | − | − | − | − | − | + |

*Two of the white pigmented S. bovis isolates did not ferment inulin;
**one S. equinus isolate germ on lactose.

TABLE 3

Lactate production (mmol/l) by *S. ruminantium* (SR R1, SR R2 and SR R3) cultures after 24 h of anaerobic incubation in a broth of basal medium 10 with glucose or starch added at 0.5% a 39° C.

|  | Type A | | Type B | |
|---|---|---|---|---|
|  | Isolates → | | | |
|  | *S. ruminantium* (SR R1) | | *S. ruminantim* (SR R2 and SR R3) | |
| Carbohydrate | Glucose | Starch | Glucose | Starch |
| L-Lactate | 23.7 | 0.0 | 20.1 | 15.5 |
| D-Lactate | 0.0 | 0.0 | 19.9 | 15.1 |
| Total (mmol/l) | 23.7 | 0.0 | 40.0 | 26.6 |
| Initial pH | 6.91 | 7.20 | 6.91 | 7.20 |

TABLE 4

Lactate production (mmol/l) by *S. bovis* and *Clostridium*-like *vitulinus* cultures after 24 h of anaerobic incubation in a broth of basal medium 10 with glucose or starch added at 0.5% at 39° C. The pH of BM 10 with glucose was 6.92 and with starch was 7.20.

| Isolates Carbo- | *S. bovis*\* (Sb R1, Sb R2, Sb R3) | | *C*-like *vitulinus* (LV R1, LV R2, LV R4, LV R5) | | *C*-like *vitulinus* (LV R3) | |
|---|---|---|---|---|---|---|
| hydrate | Glucose | Starch | Glucose | Starch | Glucose | Starch |
| L-Lactate | 41.1 | 42.2 | 0.0 | 0.0 | 20.7 | 0.0 |
| D-Lactate | 0.0 | 0.0 | 39.3 | 0.0 | 20.6 | 0.0 |
| Total (mmol/l) | 41.1 | 42.8 | 39.3 | 0.0 | 41.3 | 0.0 |

\*Mean values ± SE.

TABLE 5

Effect of virginiamycin (VM) concentration on the growth of different bacterial isolates of *S. bovis*, *Clostridium*-like *vitulinus* and *S. ruminantium* in a broth of medium 10 with glucose added at 0.5%.

| | VM level (μg/ml) Bacterial isolate | | | | | | | | | |
|---|---|---|---|---|---|---|---|---|---|---|
| | 0 | | 2 | | 4 | | 6 | | 8 | |
| Incubation period (h) → | 24 | 48 | 24 | 48 | 24 | 48 | 24 | 48 | 24 | 48 |
| *S. bovis* and *S. equinus* (orange pigmented) | + | + | − | − | − | − | − | − | − | − |
| *S. bovis* and *S. equinus* (white pigmented) | + | + | − | − | − | − | − | − | − | − |
| *Clostridium*-like *vitulinus* (LV R1) | + | + | − | + | − | + | − | + | − | + |
| *Clostridium*-like *vitulinus* (LV R2) | + | + | + | + | − | + | − | − | − | − |
| *Clostridium*-like *vitulinus* (LV R3) | + | + | + | + | − | + | − | + | − | + |
| *Clostridium*-like *vitulinus* (LV R4) | + | + | + | + | + | + | − | + | − | + |
| *Clostridium*-like *vitulinus* (LV R5) | + | + | − | + | − | + | − | + | − | − |
| *S. ruminantium* (SR R1, SR R2 and SR R3) | + | + | + | + | + | + | + | + | + | + |

\*24-h incubation, \*\*48+ h incubation.

REFERENCES

Aihua Liu (1999) Reducing the risk of lactic acidosis in sheep by probiotic lactate utilising and starch fermenting bacteria. PhD Thesis, University of New England, Armidale, NSW 2351, Australia.

Altschul, S. F., Gish W., Miller W., Myers E. W., and Lipman d. J. (1990). Basic local alignment search tool. Journal of Molecular Biology 215, 403–410.

Bryant M. P. 1956. The characteristics of strains of *Selenomonas* as isolated from bovine rumen contents. Journal of Bacteriology 72, 162–167.

Caldwell D. R. and Bryant M. P. 1966. Medium without rumen fluid for nonselective enumeration and isolation of rumen bacteria. Applied Microbiology 14, 794–801.

Courtney D. A. and Seirer R. C. 1996. Supplementary feeding o fgrain to cattle with virginiamycin to reduce th risk of acidosis. Animal Production in Australia 21, 344.

De Man J. C., Rogosa M. and Sharp M. E. 1960. A medium for the cultivation of lactobacilli. Journal of Applied Bacteriology 23, 130–135.

Dojka, M. A., Hugenholtz, P., Haack S. K., and Pace N. R. (1998). Microbial diversity in a hydrocarbon- and chlorinated-solvent-contaminated aquifer undergoing intrinsic biomediation. Applied and Environmental Microbiology 64, 3869–3877.

Godfrey S. I. Roe J. B. Speijers E. J. and Toon W. 1993. Lupin, barley, or barley plus virginiamycin as supplement for sheep at different feeding intervals. Australian Journal of Experimental Agricultural 33, 135–140.

Godfrey, S. I., Rowe J. B., Thorniley G. R., Boyce G. R. and Speijers E. J. 1995. Virginiamycin to protect sheep fed wheat, barley or oats from grain poisoning under simulated drought feeding conditions. Australian Journal of Agricultural Research 46, 393–401.

Hardie J. M. 1986. Other streptococci. In: Bergey's Manual of Systematic Bacteriology, Volume 2, Ed.: Peter H. A. Sneath, pp. 1068–1069. Williams & Wilkins. Baltimore, USA.

Huntington G. B. 1993. Nutritional problems related to the gastro-intestinal tract: Acidosis. In: D. C. Church (Ed.) The ruminant animal. Digestive physiology and nutrition. pp. 474–480. Waveland Press, Inc. Illinois, U.S.A.

JETCAR (1999) The use of antibiotics in food-producing animals: antibiotic-resistant bacteria in animals and humans. Report of the Joint Advisory Committee on Antibiotic Resistance. Commonwealth of Australia [ISBN 1 86496 061 2]

Lane, D. J. (1991), 16S/23S sequencing. In: Nucleic Acids Techniques in Bacterial Systematics, Eds.: Stackebrandt, E. and Goodfellow, M. pp. 115–175, John Wiley and Sons, New York.

Leelde, J. A. T. (1990) Ruminal Bacterium for preventing acute lactic acidosis. U.S. Pat. No. 487,941, EP594590.

Mori, Y., Takahashi, T., Katsumi, M., Katoh, K., Hiramune, T. and Kikuchi, N. 1997, Phylogenetic analyses of swine isolates of *Spectrococcus dysgalacitae* based on 16S rDNA sequence (unpublished, submitted to the DDBJ/EMBL/GenBank database on Mar. 31, 1997, Accession AB002482).

Magaraja T. G., Avery T. B., Bartley E. E., Galitzer S. J. and Dayton A. D. 1981. Prevention of lactic acidosis in cattle by lasalocid or monensin. Journal of Animal Science 53 (1), 206–216.

Nagaraja T. G., Avery T. B., Galitzer S. J. and Harmon D. L. 1985. Effect of ionophore antibiotics on experimentally induced lactic acidosis in cattle. American Journal of Veterinary Research 46 (12), 2444–2452.

Nagaraja T. G. and Taylor M. B. 1987. Susceptibility and resistance of ruminal bacteria to antimicrobial feed additives. Applied and Environmental Microbiology 53, 1620–1625.

Nagaraja T. G., Godfrey S. I., Winslow S. W. and Rowe J. B. 1995. Responses in ciliated protozoa and rumen fermentation in sheep with barley plus virginiamycin. Australian Journal of Agricultural Research 46, 1137–1147.

Nelms, L. F., Odelson, D. A., Whitehead, T. R. and Hespell, R. B. 1995. Differentiation of ruminal and human *Streptococcus bovis* strains by DNA homology and 16s rRNA probes. Current Microbiology 31, 294–300.

Rogers, J. A., Branine M. E., Miller C. R., Wray M. I., Bartle S. J., Preston R. I., Gill D. R., Pritchard R. H., Stilborn R. P. and Bechtol D. T. 1995. Effects of dietary virginiamycin on performance and liver abscess incidence in feedlot cattle. Journal of Animal Science 73, 9–20.

Rowe, J. B. 1997. 'Acidic gut syndrome.' It is a problem for animals and humans? In: Recent Advances in Animal Nutrition in Australia (eds. J. L. Corbett, M. Choct, J. V. Nolan, J. B. Rowe). pp. 47–55.

Russell, J. B. and Baldwin, R. L. 1978. Substrate preference in rumen bacteria: evidence of catabolite regulatory mechanisms. Applied and Environmental Microbiology 36, 319–329.

Russel, J. B. and Baldwin, R. L. 1979. Comparison of maintenance energy expenditures and growth yileds among several bacteria grown on continuous culture. Applied and Environmental Microbiology 37, 537–543.

Strunk, O., Gross O., Reichel B., May M., Herman S., Struckmann N., Nonhoff B., Lenke M., Vilbig A., Ludwig T., Bode A., Schleifer K-H, and Ludwig W. Program available from http://www.mikro.biologie.tu-muenchen.de (Unpublished).

Thorniley G. R.; Rose J. B.; Cowcher P. C. and Boyce M. D. 1998. A single drench of virginiamycin to increase safety of feeding grain to sheep. Australian Journal of Agricultural Research 49, 899–906.

Wallace R. J. 1996. Rumen microbiology and efficiency of digestion. In: Milk composition, production and biotechnology. Biotechnology in agricultural series 18, 465–487.

Yanke L. J. and Cheng K.-J. 1998. A method for the selective enumeration and isolation of ruminal *Lactobacillus* and *Streptococcus*. Letters in Applied Microbiology 26, 248–252.

What is claimed is:

1. A vaccine comprising at least one isolated microorganism or living or dead cells thereof wherein the microorganism is selected from the group consisting of: (a) *Streptococcus bovis* strain SbR1 Accession number NM99/04455, (b) *Streptococcus equinus* strain SER1 Accession number: NM99/04456, (c) *Streptococcus equinus* strain SER2 Accession number: NM99/04457, (d) *Selenomonas ruminantium* strain SRR1 Accession number: NM99/04458, (e) *Selenomonas ruminantium* strain SRR3 Accession number: NM99/04460, (f) *Clostridium vitulinus* strain LVR3 Accession number: NM99/04461, (g) *Clostridium vitulinus* strain LVR4 Accession number: NM99/04462, (h) *Prevotella* isolates LAB01 Accession number: NM00/12630, (i) *Prevotella* isolate LAB03 Accession number: NM00/12632, (j) *Bacteroides* isolates LAB07 Accession Number: NM00/12636, (k) *Bacteroides* isolate LAB05 Accession number: NM00/12634, (l) non-dextran slime producing *Streptococcus* isolate LAB04 Accession number: NM00/12633, (m) non-slime producing lactic acid bacterial isolates LAB02 Accession number: NM00/12631, (n) non-slime producing lactic acid bacterial isolate LAB06 Accession number: NM00/12635, and (o) non-slime producing lactic acid bacterial isolate LAB08 Accession number: NM00/12637.

2. The vaccine of claim 1, wherein said dead cells are intact cells.

3. The vaccine of claim 1, wherein the vaccine is formulated for administration via intramuscular, subcutaneous, or inhalation routes.

4. A pharmaceutical composition comprising the vaccine composition of claim 1 and a pharmaceutically acceptable carrier, adjuvant and/or diluent, wherein said pharmaceutical composition is effective for the prevention of lactic acidosis in said monogastric, herbivore, or ruminant animal.

5. The pharmaceutical composition according to claim 4, further comprising at least one cytokine.

6. A method for inducing an immune response against lactic acidosis in a vertebrate, comprising administering to said vertebrate an immunologically effective amount of the pharmaceutical composition according to claim 4.

7. A method for the treatment and/or prophylaxis of lactic acidosis in a vertebrate in need of said treatment and/or prophylaxis, wherein said method comprises administering intramuscularly, subcutaneously, or via inhalation to said vertebrate a therapeutically effective amount of a pharmaceutical composition according to claim 4.

8. A method for inducing an immune response against lactic acidosis in a vertebrate, comprising administering intramuscularly, subcutaneously, or via inhalation to said vertebrate an immunologically effective amount of the vaccine in accordance with claim 1.

9. The method according to claim 8, further comprising administering at least one cytokine.

10. A method for the treatment and/or prophylaxis of lactic acidosis in a vertebrate in need of said treatment and/or prophylaxis, wherein said method comprises administering intramuscularly, subcutaneously, or via inhalation to said vertebrate a therapeutically effective amount of the vaccine in accordance with claim 1.

11. The method of claim 10, wherein said method further comprises the administration of an active agent, wherein said active agent is selected from the group consisting of: antibiotics, enzyme preparations, clay preparations, compounds which slow the digesta flow, prebiotics and probiotics.

12. An isolated culture of at least one microorganism selected from the group consisting of: (a) *Streptococcus bovis* strain SbR1 Accession number NM99/04455, (b) *Streptococcus equinus* strain SER1 Accession number: NM99/04456, (c) *Streptococcus equinus* strain SER2 Accession number: NM99/04457, (d) *Selenomonas ruminantium* strain SRR1 Accession number: NM99/04458, (e) *Selenomonas ruminantium* strain SRR3 Accession number: NM99/04460, (f) *Clostridium vitulinus* strain LVR3 Accession number: NM99/04461, (g) *Clostridium vitulinus* strain LVR4 Accession number: NM99/04462, (h) *Prevotella* isolates LAB01 Accession number: NM00/12630, (i) *Prevo-*

*tella* isolate LAB03 Accession number: NM00/12632, (j) *Bacteroides* isolates LAB07 Accession Number: NM00/12636, (k) *Bacteroides* isolate LAB05 Accession number: NM00/12634, (l) non-dextran slime producing *Streptococcus* isolate LAB04 Accession number: NM00/12633, (m) non-slime producing lactic acid bacterial isolates LAB02 Accession number: NM00/12631, (n) non-slime producing lactic acid bacterial isolate LAB06 Accession number: NM00/12635, and (o) non-slime producing lactic acid bacterial isolate LAB08 Accession number: NM00/12637.

* * * * *

SEQUENCE LISTING

```
<160> NUMBER OF SEQ ID NOS: 15

<210> SEQ ID NO 1
<211> LENGTH: 13
<212> TYPE: PRT
<213> ORGANISM: Artificial Sequence
<220> FEATURE:
<223> OTHER INFORMATION: Synthetic peptide with high affinity for
      melanocortin receptor 1

<400> SEQUENCE: 1

Ser Ser Ile Ile Ser His Phe Arg Trp Gly Lys Pro Val
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Synthetic peptide with high affinity for
      melanocortin receptor 1
<221> NAME/KEY: MOD_RES
<222> LOCATION: (7)..(7)
<223> OTHER INFORMATION: D amino acid

<400> SEQUENCE: 2

Ser Ser Ile Ile Ser His Phe Arg Trp Gly Lys Pro Val
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Synthetic peptide with high affinity for
      melanocortin receptor 1

<400> SEQUENCE: 3
```

Tyr Ser Ser Ile Ile Ser His Phe Arg Trp Gly Lys Pro Val
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Synthetic peptide with high affinity for
      melanocoritn receptor 1

<400> SEQUENCE: 4

Tyr Ser Ile Ile Ser His Phe Arg Trp Gly Lys Pro Val
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Synthetic peptide with high affinity for
      melanocortin receptor 1

<400> SEQUENCE: 5

Ser Ser Ile Ile Ser His Phe Arg Trp Gly Lys Pro Val Tyr
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic peptide with high affinity for
      melanocortin receptor 1

<400> SEQUENCE: 6

Ser Ile Ile Ser His Phe Arg Trp Gly Lys Pro Val
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Synthetic peptide with high affinity for
      melanocortin receptor 1

<400> SEQUENCE: 7

Thr Ser Ile Ile Ser His Phe Arg Trp Gly Lys Pro Val
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Synthetic peptide with high affinity for
      melanocortin receptor 1

<400> SEQUENCE: 8

Ser Thr Ile Ile Ser His Phe Arg Trp Gly Lys Pro Val
1               5                   10

<210> SEQ ID NO 9
<211> LENGTH: 13
<212> TYPE: PRT
<213> ORGANISM: Artificial Sequence -continued

```
<220> FEATURE:
<223> OTHER INFORMATION: Synthetic peptide with high affinity for
      melanocortin receptor 1

<400> SEQUENCE: 9

Ser Ser Val Ile Ser His Phe Arg Trp Gly Lys Pro Val
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Synthetic peptide with high affinity for
      melanocortin receptor 1

<400> SEQUENCE: 10

Ser Ser Ile Val Ser His Phe Arg Trp Gly Lys Pro Val
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Synthetic peptide with high affinity for
      melanocortin receptor 1
<221> NAME/KEY: MOD_RES
<222> LOCATION: (1)..(1)
<223> OTHER INFORMATION: ACETYLATION

<400> SEQUENCE: 11

Ser Ser Ile Ile Ser His Phe Arg Trp Gly Lys Pro Val
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Synthetic peptide with high affinity for
      melanocortin receptor 1
<221> NAME/KEY: MOD_RES
<222> LOCATION: (1)..(1)
<223> OTHER INFORMATION: D amino acid

<400> SEQUENCE: 12

Ser Ser Ile Ile Ser His Phe Arg Trp Gly Lys Pro Val
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Synthetic peptide with high affinity for
      melanocortin receptor 1
<221> NAME/KEY: MOD_RES
<222> LOCATION: (1)..(1)
<223> OTHER INFORMATION: N-Methyl-L-Serine

<400> SEQUENCE: 13

Ser Ser Ile Ile Ser His Phe Arg Trp Gly Lys Pro Val
1               5                   10

<210> SEQ ID NO 14
<211> LENGTH: 13
<212> TYPE: PRT
<213> ORGANISM: Artificial Sequence
```

```
-continued

<220> FEATURE:
<223> OTHER INFORMATION: Synthetic peptide with high affinity for
      melanocortin receptor 1
<221> NAME/KEY: MOD_RES
<222> LOCATION: (13)..(13)
<223> OTHER INFORMATION: MeVal

<400> SEQUENCE: 14

Ser Ser Ile Ile Ser His Phe Arg Trp Gly Lys Pro Val
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Synthetic peptide with high affinity for
      melanocortin receptor 1
<221> NAME/KEY: MOD_RES
<222> LOCATION: (7)..(7)
<223> OTHER INFORMATION: N-Methyl-D-Phenylalanine

<400> SEQUENCE: 15

Ser Ser Ile Ile Ser His Phe Arg Trp Gly Lys Pro Val
1               5                   10
```